US006506418B1

(12) United States Patent
McKinnie et al.

(10) Patent No.: US 6,506,418 B1
(45) Date of Patent: *Jan. 14, 2003

(54) CONCENTRATED AQUEOUS BROMINE SOLUTIONS AND THEIR PREPARATION

(75) Inventors: Bonnie G. McKinnie, Magnolia, AR (US); Alvin E. Harkins, Jr., Baton Rouge, LA (US); Robert M. Moore, Jr., Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/732,601

(22) Filed: Dec. 7, 2000

Related U.S. Application Data

(63) Continuation-in-part of application No. 09/506,911, filed on Feb. 18, 2000, which is a continuation-in-part of application No. 09/456,781, filed on Dec. 8, 1999, which is a continuation-in-part of application No. 09/451,319, filed on Nov. 30, 1999, which is a continuation-in-part of application No. 09/404,184, filed on Sep. 24, 1999, now Pat. No. 6,322,822.

(51) Int. Cl.$^7$ .................... A01N 39/00; A01N 59/02; A01N 59/08; A01N 59/00
(52) U.S. Cl. .................... 424/703; 424/615; 424/663; 424/665; 424/680; 424/723
(58) Field of Search ............... 424/703, 615, 424/663, 665, 680, 723

(56) References Cited

U.S. PATENT DOCUMENTS

| | | | |
|---|---|---|---|
| 3,152,073 A | 10/1964 | Morton ..................... 210/62 |
| 3,170,883 A | 2/1965 | Owen et al. .............. 252/187 |
| 3,308,062 A | 3/1967 | Gunther ..................... 210/58 |
| 3,328,294 A | 6/1967 | Self et al. .................. 210/62 |
| 3,558,503 A | 1/1971 | Goodenough et al. ...... 252/187 |
| 3,589,859 A | 6/1971 | Foroulis ..................... 21/2.7 |
| 3,711,246 A | 1/1973 | Foroulis ..................... 21/2.7 |
| 3,749,672 A | 7/1973 | Golton et al. .............. 252/95 |
| 3,767,586 A | 10/1973 | Rutkiewic ............. 252/187 H |
| 4,032,460 A | 6/1977 | Zilch et al. ........... 252/8.55 B |
| 4,237,090 A | 12/1980 | DeMonbrun et al. ......... 422/13 |
| 4,295,932 A | 10/1981 | Pocius ..................... 162/161 |
| 4,382,799 A | 5/1983 | Davis et al. .................. 8/107 |
| 4,427,435 A | 1/1984 | Lorenz et al. ............... 71/67 |
| 4,451,376 A | 5/1984 | Sharp ....................... 210/701 |
| 4,465,598 A | 8/1984 | Darlington et al. ......... 210/721 |
| 4,476,930 A | 10/1984 | Watanabe .................. 166/279 |
| 4,490,308 A | 12/1984 | Fong et al. ............. 260/513 N |
| 4,539,071 A | 9/1985 | Clifford et al. ............. 162/161 |
| 4,546,156 A | 10/1985 | Fong et al. ................. 526/240 |
| 4,566,973 A | 1/1986 | Masler, III et al. ......... 210/701 |
| 4,595,517 A | 6/1986 | Abadi ......................... 252/82 |
| 4,595,691 A | 6/1986 | LaMarre et al. ............ 514/367 |
| 4,604,431 A | 8/1986 | Fong et al. ................. 525/351 |
| 4,642,194 A | 2/1987 | Johnson ..................... 210/699 |
| 4,643,835 A | 2/1987 | Koeplin-Gall et al. ...... 210/754 |
| 4,661,503 A | 4/1987 | Martin et al. .............. 514/372 |
| 4,680,339 A | 7/1987 | Fong ........................ 525/54.11 |
| 4,680,399 A | 7/1987 | Buchardt ................... 546/139 |
| 4,703,092 A | 10/1987 | Fong ......................... 525/351 |
| 4,711,724 A | 12/1987 | Johnson ..................... 210/699 |
| 4,752,443 A | 6/1988 | Hoots et al. .................. 422/13 |
| 4,759,852 A | 7/1988 | Trulear ....................... 210/699 |
| 4,762,894 A | 8/1988 | Fong et al. ................. 525/344 |
| 4,777,219 A | 10/1988 | Fong ........................ 525/329.4 |
| 4,801,388 A | 1/1989 | Fong et al. ................. 210/701 |
| 4,802,990 A | 2/1989 | Inskeep, Jr. ................ 210/699 |
| 4,822,513 A | 4/1989 | Corby ........................ 252/106 |
| 4,846,979 A | 7/1989 | Hamilton .................... 210/754 |
| 4,883,600 A | 11/1989 | MacDonald et al. ........ 210/696 |
| 4,886,915 A | 12/1989 | Favstritsky ................. 564/503 |
| 4,898,686 A | 2/1990 | Johnson et al. .......... 252/389.2 |
| 4,906,651 A | 3/1990 | Hsu ........................... 514/372 |
| 4,923,634 A | 5/1990 | Hoots et al. ............. 252/389.2 |
| 4,929,424 A | 5/1990 | Meier et al. ................... 422/9 |
| 4,929,425 A | 5/1990 | Hoots et al. .................. 422/13 |
| 4,966,716 A | 10/1990 | Favstritsky et al. ......... 210/755 |
| 4,992,209 A | 2/1991 | Smyk et al. ................ 252/387 |

(List continued on next page.)

FOREIGN PATENT DOCUMENTS

| | | |
|---|---|---|
| WO | 9015780 | 12/1990 |
| WO | 9720546 | 6/1997 |
| WO | 9720909 | 6/1997 |
| WO | 9734827 | 9/1997 |
| WO | 9743392 | 11/1997 |
| WO | 9815609 | 4/1998 |
| WO | 9906320 | 2/1999 |
| WO | 9932596 | 7/1999 |
| WO | 9955627 | 11/1999 |
| WO | 0034186 | 6/2000 |
| WO | 00/34186 | 6/2000 |

OTHER PUBLICATIONS

Ault et al., "Infrared and Raman Spectra of the M+Cl$_3^-$ ion Pairs and Their Chlorine–bromine Counterparts isolated in Argon Matrices", Journal of Chemical Physics, 1976, vol. 64, No. 12, pp. 4853–4859.

Willard et al., "Elementary Quantitative Analysis", Third Edition, Chapter XIV, 1933, pp. 261–271.

Primary Examiner—Alton Pryor
(74) Attorney, Agent, or Firm—Edgar E. Spielman, Jr.

(57) ABSTRACT

Concentrated liquid biocide compositions are produced by: A) feeding (a) bromine atoms and chlorine atoms in the form of (i) one or more of BrCl, (ii) Br$_2$, and (iii) Cl$_2$ into (b) water containing sulfamate anions, or feeding each of (a) and (b) into a reaction vessel, such that the numerical ratio of the total number of bromine atoms fed to the total number of chlorine atoms fed is in the range of about 0.7:1 to about 1.7:1; and B) providing enough alkali metal base in the mixture being formed in A) to keep the pH of such mixture in the range of about 7–11 during all or substantially all of the time feeding in A) is occurring, the amounts of (a) and (b) used being amounts that form an active-bromine-containing solution in which (i) the active bromine content is 50,000 ppm or more, and (ii) the atom ratio of nitrogen to active bromine originating from (a) and (b) is greater than about 0.93; and wherein if any sulfate is present in the solution as formed, the molar ratio of sulfate to sulfamate in the solution is less than about 0.2.

61 Claims, 3 Drawing Sheets

U.S. PATENT DOCUMENTS

| | | | |
|---|---|---|---|
| 4,995,987 A | 2/1991 | Whitekettle et al. | 210/754 |
| 5,034,155 A | 7/1991 | Soeder et al. | 252/389.23 |
| 5,035,806 A | 7/1991 | Fong et al. | 210/701 |
| 5,047,164 A | 9/1991 | Corby | 252/106 |
| 5,055,285 A | 10/1991 | Duncan et al. | 423/473 |
| 5,118,426 A | 6/1992 | Duncan et al. | 210/721 |
| 5,120,452 A | 6/1992 | Ness et al. | 210/754 |
| 5,120,797 A | 6/1992 | Fong et al. | 525/329.4 |
| 5,141,652 A | 8/1992 | Moore, Jr. et al. | 210/754 |
| 5,179,173 A | 1/1993 | Fong et al. | 525/329.4 |
| 5,192,459 A | 3/1993 | Tell et al. | 252/106 |
| 5,194,238 A | 3/1993 | Duncan et al. | 423/473 |
| 5,196,126 A | 3/1993 | O'Dowd | 210/754 |
| 5,202,047 A | 4/1993 | Corby | 252/106 |
| 5,259,985 A | 11/1993 | Nakanishi et al. | 252/180 |
| 5,264,136 A | 11/1993 | Howarth et al. | 210/754 |
| 5,389,384 A | 2/1995 | Jooste | 424/661 |
| 5,414,652 A | 5/1995 | Mieda et al. | 365/122 |
| 5,424,032 A | 6/1995 | Christensen et al. | 422/14 |
| 5,443,849 A | 8/1995 | Corby | 424/667 |
| 5,464,636 A | 11/1995 | Hight et al. | 424/661 |
| 5,525,241 A | 6/1996 | Clavin et al. | 210/753 |
| 5,527,547 A | 6/1996 | Hight et al. | 424/661 |
| 5,589,106 A | 12/1996 | Shim et al. | 252/387 |
| 5,607,619 A | 3/1997 | Dadgar et al. | 252/187.2 |
| 5,679,239 A | 10/1997 | Blum et al. | 205/556 |
| 5,683,654 A | 11/1997 | Dallmier et al. | 422/14 |
| 5,795,487 A | 8/1998 | Dallimier et al. | 210/754 |
| 5,900,512 A | 5/1999 | Elnagar et al. | 568/14 |
| 5,922,745 A | 7/1999 | McCarthy et al. | 514/372 |
| 5,942,126 A | 8/1999 | Dallmier et al. | 210/756 |
| 6,007,726 A | 12/1999 | Yang et al. | 210/752 |
| 6,015,782 A | 1/2000 | Petri et al. | 510/379 |
| 6,037,318 A | 3/2000 | Na et al. | 510/379 |
| 6,068,861 A * | 5/2000 | Moore et al. | 424/703 |
| 6,110,387 A * | 8/2000 | Choudhury et al. | 210/752 |
| 6,123,870 A | 9/2000 | Yang et al. | 252/186.1 |
| 6,156,229 A | 12/2000 | Yang et al. | 252/186.1 |
| 6,270,722 B1 | 8/2001 | Yang et al. | 422/37 |
| 6,287,473 B1 | 9/2001 | Yang et al. | 210/754 |

* cited by examiner

CONCENTRATED AQUEOUS BROMINE SOLUTIONS AND THEIR PREPARATION

REFERENCE TO RELATED APPLICATIONS

This is a continuation-in-part of commonly-owned application Ser. No. 09/404,184, filed Sep. 24, 1999, is now U.S. Pat. No. 6,322,833 Ser. No. 09/451,319, filed Nov. 30, 1999; Ser. No. 09/456,781, filed Dec. 8, 1999; and Ser. No. 09/506,911, filed Feb. 18, 2000, the entire disclosures of each of which to the extent not in conflict with the present application, are incorporated herein by reference.

REFERENCE TO OTHER COMMONLY-OWNED APPLICATIONS

Reference is also made to commonly-owned copending 09/442,025, filed Nov. 17, 1999; Ser. No. 09/451,344, filed Nov. 30, 1999; Ser. No. 09/663,788, filed Sep. 18, 2000; and Ser. No. 09/663,948, filed Sep. 18, 2000. The entire disclosures of each of the foregoing four (4) applications to the extent not in conflict with the present application, are incorporated herein by reference. Reference is also made to commonly-owned copending Application Ser. Nos. 09/296,499, filed Apr. 22, 1999; and Ser. No. 09/658,839, filed Sep. 8, 2000.

All of the applications referred to above relate to aqueous biocidal bromine solutions and/or their preparation or use.

BACKGROUND

Bromine-based biocides have proven biocidal advantages over chlorination-dechlorination for the microbiological control of cooling waters and disinfection of waste treatment systems. The water treatment industry recognizes these advantages to be cost-effective control at higher pH values, almost no loss in biocidal activity in the presence of ammonia, and effective control of bacteria, algae and mollusks.

A common way of introducing bromine-based biocides into a water system is through the use of aqueous NaBr in conjunction with NaOCl bleach. The user feeds both materials to a common point whereupon the NaOCl oxidizes the bromide ion to $HOBr/OBr^{\ominus}$. This activated solution is then introduced directly into the water system to be treated. The feeding of the two liquids in this fashion is necessary because the $HOBr/OBr^{\ominus}$ mixture is unstable and has to be generated on-site just prior to its introduction to the water. Furthermore, the feeding, and metering of two liquids is cumbersome, especially as the system has to be designed to allow time for the activation of bromide ion to occur. Consequently many biocide users have expressed the need for a single-feed, bromine-based biocide. Elemental bromine and molecular bromine chloride have been considered to meet these demands. Both are liquids at room temperature and can be fed directly to the water system, where immediate hydrolysis occurs to yield HOBr.

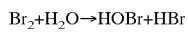  (1)

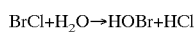  (2)

Properties of bromine and bromine chloride are compared in Table 1.

TABLE 1

Physical Properties of Bromine and Bromine Chloride

| Property | Bromine ($Br_2$) | Bromine Chloride (BrCl) |
|---|---|---|
| Appearance | Fuming, dark-red liquid | Fuming, red liquid or gas |
| Boiling Point | 59° C. | 5° C. |
| Vapor Pressure (25° C.) | 214 mm | 1800 mm |
| Corrosivity | Corrodes most metals in the presence of water | Corrodes most metals in the presence of water |

It can be seen that certain characteristics of these materials—especially their corrosiveness, high vapor pressures and fuming tendencies—necessitate care and skill in their handling and use. Early efforts to overcome the deficiencies of these materials comprised complexing bromine with excess bromide ion in the presence of strong acid and stabilizing the resultant solutions with ethanolamine. The resultant solutions of ethanolammonium hydrogen perbromide contained up to 38% by weight elemental bromine. See in this connection, Favstritsky, U.S. Pat. No. 4,886,915; and Favstritsky, Hein, and Squires, U.S. Pat. No. 4,966,716.

These solutions permitted introduction of bromine to a water system using a single feed. As in the case of bromine and bromine chloride, the ethanolammonium hydrogen perbromide hydrolyzed in water to release HOBr. The vapor pressures of these solutions were lower than elemental bromine and bromine chloride. Nevertheless, the solutions still possessed measurable vapor pressures, and thus tended to produce undesirable reddish-colored vapors during storage and use.

An economically acceptable way of stabilizing high concentrations of aqueous solutions of bromine chloride is described in U.S. Pat. No. 5,141,652 to Moore, et al. The solution is prepared from bromine chloride, water and a halide salt or hydrohalic acid. These solutions were found to decompose at a rate of less than 30% per year and in cases of high halide salt concentration, less than 5% per year. Moreover, solutions containing the equivalent of 15% elemental bromine could be prepared. Unfortunately, the relatively high acidity of these solutions and their tendency to be corrosive and fuming impose limitations on their commercial acceptance.

Many solid bromine derivatives such as BCDMH (N,N-bromochloro-5,5-dimethylhydantoin) are limited in the amount of material that can be dissolved in water and fed as a liquid to the water treatment system. For example, the solubility of BCDMH in water is only around 0.15%. Another limitation of such derivatives is that at neutral pH, HOBr rapidly decomposes, eventually forming bromide ions. Thus, the ability to store and transport these aqueous solutions is greatly limited and of questionable commercial feasibility.

U.S. Pat. No. 3,558,503 to Goodenough et al. describes certain aqueous bromine solutions stabilized with various stabilizing agents and various uses to which such solutions can be put. The compositions described in the patent comprise an aqueous bromine solution having from about 0.01 to about 100,000 parts per million by weight of bromine values wherein the molar ratio of bromine to nitrogen present in the bromine stabilizer ranges from about 2.0 to 1 to about 0.5 to 1. The stabilizer used is biuret, succinimide, urea, a lower aliphatic mono- or disubstituted urea containing from about 2 to about 4 carbon atoms in each substituent group, sulfamic acid, or an alkyl sulfonamide of the formula $RSO_3NH_2$ where R is a methyl or ethyl group. The solution also contains sufficient hydroxide additive to provide a pH in the solution ranging from about 8 to about 10, the hydroxide additive being an alkaline earth hydroxide or an alkali metal hydroxide.

U.S. Pat. No. 5,683,654 to Dalhnier et al. discusses the preparation of aqueous alkali metal or alkaline earth metal hypobromite solutions by mixing an aqueous solution of alkali or alkaline earth metal hypochlorite with a water soluble bromide ion source to form a solution of unstabilized alkali or alkaline earth metal hypochlorite. To this solution is added an aqueous solution of an alkali metal sulfamate having a temperature of at least 50° C. and in an amount that provides a molar ratio of alkali metal sulfamate to alkali or alkaline earth metal hypobromite of from about 0.5 to about 6 whereby a stabilized aqueous alkali or alkaline earth metal hypobromite solution is formed. The Dallmier et al. patent teaches that much higher levels of available halogen for disinfection were attained by this approach as compared to the Goodenough et al. approach. But the Dallmier et al. patent acknowledges that in their process, the stabilization must occur quickly after the unstable NaOBr is formed.

U.S. Pat. No. 5,795,487 to Dallmier et al. describes amethod for preparing a stabilized alkali or alkaline earth metal hypobromite solution. The method comprises mixing an aqueous solution of alkali or alkaline earth metal hypochlorite having about 5–70% of available halogen as chlorine with a water-soluble bromide ion source, allowing the bromide ion source and the hypochlorite to react to form a 0.5–70 wt % aqueous solution ofunstabilized alkali or alkaline earth metal hypobromite, adding to this unstabilized solution an aqueous solution of an alkali metal sulfamate in amount to provide a molar ratio of alkali metal sulfamate to alkali or alkaline earth metal hypobromite of from about 0.5 to about 0.7, and recovering a stabilized aqueous alkali or alkaline earth metal hypobromite solution. The order of addition in the process is said to be critical.

U.S. Pat. No. 6,007,726 to Yang et al. describes the formation of stabilized bromine formulations. In that process, a solution of alkali or alkaline earth metal bromide and an halogen stabilizer such as sulfamic acid is formed and adjusted to a pH of about 4 to about 8. To this solution is added ozone, a peroxide, or a peracid such as peracetic acid, to generate an oxidizing bromine compound in the solution. The pH of the solution can then be raised to 13 or above. The process is demonstrated by use of ozone from an ozonator, and it is indicated that it is important to maintain a high reaction pH and a low reaction temperature to keep the stable oxidizing bromines from thermally decomposing.

BRIEF SUMMARY OF THE INVENTION

Improved process technology for forming concentrated aqueous solutions of biocidally active bromine, and improved concentrated aqueous solutions of biocidally active bromine, are provided by this invention.

This invention involves, inter alia, the discovery that when producing concentrated aqueous solutions of biocidally active bromine in which sulfamate is present in the reaction mixture, suitable control of pH of the aqueous reaction mixture throughout the production process can have important beneficial effects upon both the reaction itself and the biocidally-active product being produced. For example, when producing a concentrated liquid biocide composition by mixing (a) bromine chloride, or bromine and chlorine with (b) an aqueous solution containing sulfamate anion, a substantial portion of the sulfamate can be hydrolyzed rather rapidly to sulfate under acidic conditions. Although the reaction mixture is sufficiently stable to produce a concentrated aqueous biocidal solution, loss of sulfamate due to hydrolysis to sulfate during the production process can result in decreased storage stability of the finished product even though sufficient base is introduced into the solution as the last step of the production process to raise the pH of the solution to 13 or above. Moreover, loss of sulfamate imposes an economic burden on the operation. On the other hand, use ofhighly basic reaction conditions throughout the production process can result in degradation of glass-lined reactors which are desirably employed to minimize the possibility of heavy metal extraction from metallic reactor surfaces, a possibility which is to be avoided since the biocidal solutions are primarily used in water treatment. Accordingly, pursuant to this invention the foregoing difficulties are minimized, if not eliminated.

Moreover, this invention enables economical production on an industrial scale of storage-stable aqueous concentrates which, because of the manner in which they are produced, can provide especially effective control of bacteria, algae, mollusks, and biomass.

Accordingly, pursuant to one of the embodiments of this invention there is provided a process of producing a concentrated liquid biocide composition, which process comprises:

A) bringing together in any feasible manner to form a reaction mixture (a) bromine atoms and chlorine atoms in the form of one or more of (i) bromine chloride, (ii) elemental bromine, and (iii) elemental chlorine, (b) a source of sulfamate anions, preferably an alkali metal sulfamate, and more preferably sodium sulfamate, (c) alkali metal base, preferably a sodium base, and most preferably sodium hydroxide and/or sodium oxide, and (d) water, such that the numerical ratio of bromine atoms to chlorine atoms brought to the mixture is in the range of about 0.7:1 to about 1.7:1, and preferably in the range of about 1:1 to about 1.2: 1; and B) providing before and/or during A) enough alkali metal base in the mixture being formed in A) to keep the pH of such mixture in the range of about 7 to about 11, and preferably in the range of about 8 to about 10, during all or substantially all of the time the conduct of A) is occurring, the amounts of (a), (b), (c), and (d) used being amounts that form an active-bromine-containing solution in which (i) the active bromine content is at least about 50,000 ppm (wt/wt) (i.e., at least about 5 wt % of the mixture is active bromine content), and preferably at least about 100,000 ppm (wt/wt), and more preferably at least about 120,000 ppm (wt/wt), and (ii) the atom ratio ofnitrogen to active bromine originating from (a) and (b) is greater than about 0.93, and preferably greater than 1; and wherein if any sulfate is present in the active-bromine-containing solution as formed, such sulfate content is such that the molar ratio of sulfate to sulfamate in the solution is less than about 0.2, and preferably less than about 0.05.

As used anywhere in this document, including the claims, the phrase "bringing together in any feasible manner" denotes that (a), (b), (c), and (d) can be brought together in any chemically feasible way of feeding, and that (a), (b), (c), and (d) can be brought together as individual entities and/or as one or more chemically feasible subcombination(s) of two or more of them. As any chemist or chemical engineer can readily understand, there are a considerable number of feasible ways of bringing (a), (b), (c), and (d) together in a chemically feasible way so that there is no splattering, excessive heat generation, or violent reaction when they are brought together. Suffice it to say here, that ordinary common sense from a chemical standpoint is expected to be observed both in interpreting this phrase and in implementing this phrase.

A preferred embodiment of this invention is a process of producing a concentrated liquid biocide composition, which process comprises:

A) feeding (a) bromine atoms and chlorine atoms in the form of one or more of (i) bromine chloride, (ii) elemental bromine, and (iii) elemental chlorine into (b) water containing sulfamate anions, or feeding each of (a) and (b) into a reaction vessel, such that the numerical ratio of the total number of bromine atoms fed to the total number of chlorine atoms fed is in the range of about 0.7:1 to about 1.7:1, and preferably in the range of about 1:1 to about 1.2:1; and B) providing before and/or during A) enough alkali metal base in the mixture being formed in A) to keep the pH of such mixture in the range of about 7 to about 11, and preferably in the range of about 8 to about 10, during all or substantially all of the time feeding in A) is occurring, the amounts of (a), (b), (c), and (d) used being amounts that form an active-bromine-containing solution in which (i) the active bromine content is at least about 50,000 ppm (wt/wt), and preferably at least about 100,000 ppm (wt/wt), and more preferably at least about 120,000 ppm (wt/wt), and (ii) the atom ratio of nitrogen to active bromine originating from (a) and (b) is greater than about 0.93, and preferably greater than 1; and wherein if any sulfate is present in the active-bromine-containing solution as formed, such sulfate content is such that the molar ratio of sulfate to sulfamate in the solution is less than about 0.2, and preferably less than about 0.05.

Preferably, after completing of the feeding in A) in the above processes, the pH of the active-bromine-containing solution is raised to at least about 12, and more preferably to a pH that is at least in the range of about 13 to about 13.5. Typically this is accomplished by adding additional alkali metal base to, or otherwise mixing additional alkali metal base with, the active-bromine-containing solution.

Another embodiment of this invention is a process of minimizing or eliminating loss of sulfamate during production of a sulfamate-stabilized liquid biocide composition, which process comprises:

A) feeding (a) bromine atoms and chlorine atoms in the form of one or more of (i) bromine chloride, (ii) elemental bromine, and (iii) elemental chlorine into (b) water containing sulfamate anion, or feeding each of (a) and (b) separately into a reaction vessel, or otherwise bringing (a) and the components of (b) together by feeding them in any way except feeding any of the components of (b) singly or in any combination into (a), and B) minimizing sulfate formation in the resultant aqueous solution by providing before and/or during A) enough alkali metal base in the mixture being formed in A) to keep the pH of the mixture in the range of about 7 to about 11, and preferably in the range of about 8 to about 10, during all or substantially all of the time the feeding of A) is occurring so that loss of sulfamate is minimized or eliminated. Thus if any sulfate is formed and is present, the molar ratio of sulfate to sulfamate in the concentrated liquid biocide composition as formed is typically less than about 0.2, and preferably less than about 0.05.

In conducting this embodiment it is preferred, but not essential, to proportion (a) and (b) such that numerical ratio of the total number of bromine atoms fed to the total number of chlorine atoms fed is in the range of about 0.7:1 to about 1.7:1, and preferably in the range of about 1:1 to about 1.2:1. Also, in conducting this embodiment it is preferred, but not essential, to use (a) and (b) in amounts that form an active-bromine-containing solution in which (i) the active bromine content is at least about 50,000 ppm (wt/wt), and preferably at least about 100,000 ppm (wt/wt), and more preferably at least about 120,000 ppm (wt/wt), and (ii) the atom ratio of nitrogen to active bromine originating from (a) and (b) is greater than about 0.93, and preferably greater than 1. In addition, it is preferable when conducting this embodiment to raise the pH of the aqueous solution after completing the feeding of A), to at least about 12, and more preferably to a pH that is at least in the range of about 13 to about 13.5.

As will be described more fully hereinafter, there are various ways by which the bromine atoms and chlorine atoms of (a) can be fed using members of the group consisting of bromine chloride, bromine and chlorine. For example, some of the preferred ways involve feeding (1) bromine chloride by itself, (2) bromine chloride in a mixture with bromine, or (3) bromine and chlorine fed separately and concurrently and/or fed separately and sequentially with either one being fed first.

In all of the embodiments of this invention described above, the feeds in A) can be conducted in any manner as long as the pH of the mixture being formed stays or is kept in the range of about 7 to about 11, and preferably in the range of about 8 to about 10, during all or substantially all of the time feeding in A) is occurring. For example, the feed of (a) into (b) can be continuous or intermittent, or both. Likewise the separate feeds of (a) and (b) into a reaction vessel can be continuous or intermittent, or both, and these separate feeds are concurrent or substantially concurrent feeds, and/or these separate feeds are conducted in alternating sequences. To keep the pH in the range of about 7 to about 11, and preferably in the range of about 8 to about 10, during all or substantially all of the time feeding in A) is occuring:

1) dissolved alkali metal base can be included in (b) and/or 2) a water solution of alkali metal base can be separately fed, continuously or intermittently, or both, either (i) as a feed into (b), or (ii) as a feed along with separate feeds of (a) and (b) into a reaction vessel, whichever of (i) and (ii) is being carried out in A).

In preferred embodiments, the sulfamate anion of (b) is provided by mixing together in water, (i) sulfamic acid and/or an alkali metal salt of sulfamic acid, and (ii) alkali metal base in proportions such that an aqueous solution of alkali metal salt of sulfamic acid is formed having a pH of at least 7 and preferably at least 8. If sulfamic acid itself is used as the starting material, it is used initially as a slurry in water with which the alkali metal base is mixed.

Operation in accordance with the above embodiments of this invention not only results in minimized hydrolysis of sulfamate to sulfate, but aqueous biocidal solutions produced in this manner when used in proper dosage levels provide especially effective control of bacteria, algae, mollusks, and biomass. Also, if the reaction of (a) with (b) is carried out in a glass-lined reaction vessel, the glass lining will not undergo as severe attack as it would if this entire reaction were conducted at a higher pH such as 12, 13 or 14.

Still another embodiment of this invention is a process producing a liquid biocide composition wherein the pH of the reaction mixture is controlled in at least three stages. The process of this embodiment comprises:

I) bringing together in any feasible manner to form a reaction mixture (a) bromine atoms and chlorine atoms in the form of one or more of (i) bromine chloride, (ii) elemental bromine, and (iii) elemental chlorine, (b) a source of sulfamate anions, preferably an alkali metal sulfamate, and more preferably sodium sulfamate, (c) alkali metal base, preferably a sodium base, and most preferably sodium hydroxide and/or sodium oxide, and (d) water, such that (1) the numerical ratio of bromine atoms to chlorine atoms brought into the mixture is in the range of about 0.7:1 to about 1.7:1, and preferably in the range of about 1:1 to about 1.2:1, and (2) the atom ratio of nitrogen to active bromine originating from (a) and (b) is greater than about 0.93, and preferably greater than about 1; to form an active-bromine-containing reaction product mixture that has, initially, a pH over 11, preferably at least about 12, and more preferably at least about 13;

II) providing before and/or during the conduct of I) an amount of alkali metal base in relation to the total amount of acid (HBr and/or HCl) co-product(s) to be formed in the reaction, that results in the pH of such reaction product mixture decreasing by at least 1 pH unit during the conduct of I), to a pH in the range of about 7 to about 11, and preferably to a pH in the range of about 8 to about 10;

III) keeping the reaction mixture at a pH in the range of about 7 to about 11, and preferably at a pH in the range of about 8 to about 10 for a period of time that increases the microbiocidal effectiveness of the concentrated liquid biocide composition being formed; and then IV) raising the pH of the resultant active-bromine-containing reaction product mixture to at least about 12, and preferably to a pH that is at least in the range of about 13 to about 13.5, by mixing additional alkali metal base therewith.

Among feasible ways of bringing (a), (b), (c), and (d) together per I) above are operations wherein (b), (c), and (d) are brought to the reaction mixture by feeding (b), (c), and (d) as individual entities and/or by feeding any two or all three of (b), (c) and (d) as one or more preformed mixtures of such any two or all three thereof, and operations wherein (a), (b), (c), and (d) are brought together in any chemically feasible manner of feeding. Typically, neither (b), nor (c), nor (d), singly or in any combination(s) or sub-combination (s) with each other, would be fed into (a), Yet another embodiment of this invention wherein the pH of the reaction mixture is controlled in at least three stages is a process of producing a concentrated liquid biocide composition, which process comprises:

I) feeding (a) bromine atoms and chlorine atoms in the form of one or more of (i) bromine chloride, (ii) elemental bromine, and (iii) elemental chlorine, into (b) an aqueous solution of sulfamate anions and alkali metal base, or feeding each of (a) and (b) into a reaction vessel, such that the numerical ratio of bromine atoms to chlorine atoms fed is in the range of about 0.7:1 to about 1.7:1, and preferably in the range of about 1:1 to about 1.2:1, to form an active-bromine-containing reaction product mixture that has, initially, a pH over 11, preferably at least about 12, and more preferably at least about 13;

II) providing before and/or during the feeding in I) an amount of alkali metal base in relation to the total amount of acid (HBr and/or HCl) co-product(s) to be formed in the reaction, that results in the pH of such reaction product mixture decreasing by at least 1 pH unit during the feeding in I), to a pH in the range of about 7 to about 11, and preferably to a pH in the range of about 8 to about 10;

III) keeping the reaction product mixture at a pH in the range of about 7 to about 11, and preferably at a pH in the range of about 8 to about 10, for a period of time that increases the microbiocidal effectiveness of the concentrated liquid biocide composition being produced; and then IV) raising the pH of the resultant active-bromine-containing reaction product mixture to at least about 12, and preferably to a pH that is at least in the range of about 13 to about 13.5, by mixing additional alkali metal base therewith.

Instead of performing II) as specified above, the decrease in pH pursuant to II) in each of the above processes can occur after completing the feeding in I) by using enough base to keep the pH over 11, preferably at least about 12, and more preferably at least about 13 during the feeding, and by adding to the resultant reaction mixture after completing the feeding in I), enough HBr and/or HCl to cause the pH to decrease as specified in II) above. However this is a less preferred way of operating.

If desired, operation pursuant to IV) in each of the above processes can be conducted in two or more stages of increased pH levels. However, preferably the pH is adjusted to the desired final pH value in a one-stage operation.

In each of the embodiments of this invention, the atom ratio of nitrogen based on sulfamic acid (plus alkali metal base) or alkali metal sulfamate used to active bromine is preferably greater than 1, and more preferably in the range of about 1.1 to about 1.5. Still higher ratios can be employed, if desired.

The above and other embodiments of this invention will be still further apparent from the ensuing description and appended claims.

FURTHER DETAILED DESCRIPTION OF THE INVENTION

Figure 1:
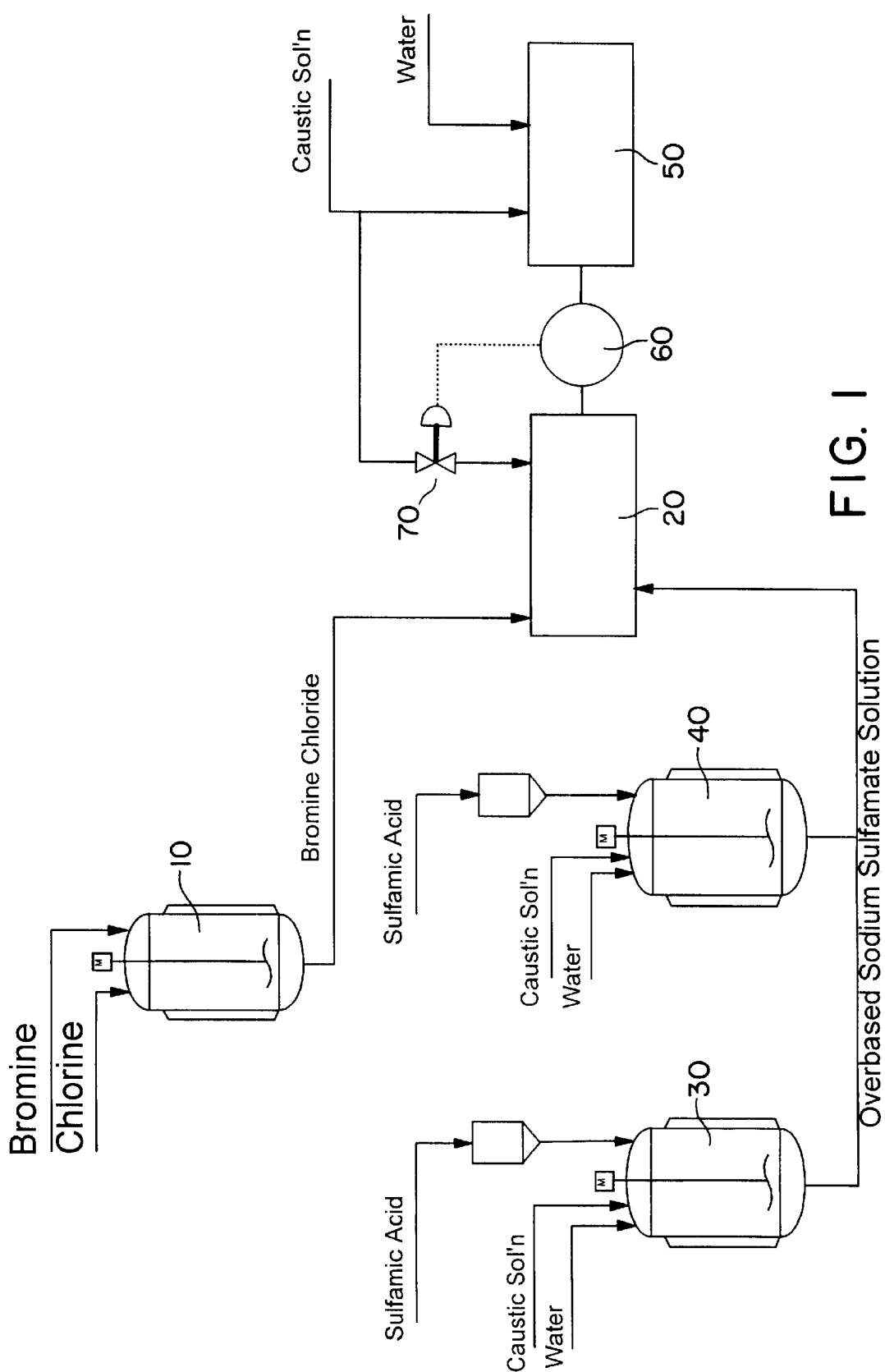
FIG. 1 is a schematic flow diagram of a plant layout suitable for the practice of continuous processes.

The embodiment involving a process producing a concentrated liquid biocide composition wherein the pH of the reaction mixture is controlled in at least three stages (hereinafter sometimes called a "Three Stage Process") involves certain special considerations, and yet also involves, in part, aspects of the other embodiments of this invention. Therefore, the details of these other embodiments are described in "PART ONE" below. The details of the Three Stage Process are set forth in "PART TWO" below.

Throughout this disclosure reference is often made to "bromine chloride", a term commonly used by chemists to describe a substance made by combining bromine and chlorine. This substance is generally represented in the chemical arts by the molecular formula BrCl or Br—Cl. We wish to forestall any quibbling based on hypertechnicalities, to make note of the fact that there is evidence to indicate that "bromine chloride" itself is an equimolar mixture of elemental bromine and elemental chlorine, and further that under ordinary conditions 100% pure Br—Cl probably does not exist as such, but rather the equimolar mixture itself apparently exists as a mixture of about 60% Br—Cl, 20% $Br_2$, and 20% $Cl_2$. But whatever it is, the substance known to chemists as "bromine chloride" is what is being referred to. And reference herein to a mixture of "bromine chloride and bromine" or a mixture of "bromine chloride and chlorine" simply means that besides the equimolar mixture of bromine and chlorine known to chemists as "bromine chloride", whatever its makeup, there is a an excess amount of bromine or chlorine, respectively, over the equimolar amount of bromine and chlorine.

PART ONE

As seen from the above, the process technology of this invention involves, in part, contacting and mixing (a) and (b) above, usually by feeding (a) into (b), or by feeding each of (a) and (b) into a reaction vessel to form one or more stabilized active bromine species, and then increasing the pH of the resultant solution to a pH of at least about 12, and preferably to a pH that is at least in the range of about 13 to about 13.5 by use of a suitable base, preferably an alkali metal base. One of the features of this process is controlling the pH to between about 7 and about 11, and preferably between about 8 and about 10, during all or substantially all of the time such feeding is taking place, and more preferably throughout or substantially throughout the time from the initiation of such feeding until the pH of the resultant solution is raised to a pH of at least about 12, and preferably to a pH that is at least in the range of about 13 to about 13.5. If the pH is allowed to fall below about 7 for any substantial period of time, hydrolysis of sulfamate to sulfate is accelerated, and the lower the pH and the longer the time the pH is below about 7, the greater the amount of such undesirable hydrolysis. Thus the pH is maintained by introducing into the solution (continuously or intermittently, as desired) additional alkali metal base, such as by a co-feed of an aqueous solution of alkali metal base. Another way of accomplishing such pH maintenance is by initially providing enough alkali metal base in the water to have the initial pH of the water at about 11 or slightly above 11 before initiating the feed of (a) into (b). Then a controlled feed of (a) is initiated. As the feed of (a) proceeds and the pH of the aqueous medium falls due to the formation of acidic species (e.g., HBr and/or HCl) in the reaction solution, sufficient alkali metal base is introduced into the solution (continuously or intermittently, as desired) before the pH drops below about 7 to keep the pH between about 7 and about 11, and preferably between about 8 and about 10, as more (a) is fed. If (a) and (b) are each being fed separately into a reaction vessel, water plus alkali metal base can be initially placed in the reaction vessel so that upon initiating the feeds of (a) and (b), the pH of the mixture being formed is at about 11 or slightly above 11. Then controlled coordinated separate feeds of (a) and (b) into the reaction vessel is initiated. Whether feeding (a) into (b) or feeding each of (a) and (b) separately into a reaction vessel, the pH of the reaction solution can be, and preferably is, monitored by use of a pH meter or other suitable pH indicator. In addition, the resultant aqueous reaction solution should be stirred or otherwise agitated to ensure thorough mixing at least during the continuance of the feeds to ensure that the pH is not only suitably controlled between about 7 and about 11, and preferably between about 8 and about 10, but that the pH of the reaction solution is uniform or substantially uniform throughout the solution.

The pH control or maintenance pursuant to this invention thus provides a number of important advantages. For example, conversions of sulfamate to sulfate are typically kept below about 5 mole percent, and the microbiocidal effectiveness of the finished biocidal solution tends to be higher than if the entire operation were conducted at a pH above about 11. Also, longer term the adverse effect upon glass-lined reaction vessels is significantly less by operating at a pH of about 11 or below as compared to operating at a higher pH such as 12, 13, or 14.

Although it is preferred that the pH be in the specified range of about 7 to about 11 or more preferably, in the range of about 8 to about 10, during all or substantially all of the time the feeding in A) is occurring, one or more brief departures from such range are permissible. The proviso here is that the magnitude and duration of any such departure(s) should not (i) substantially increase the amount of sulfamate hydrolysis to sulfate, (ii) significantly decrease the microbiocidal effectiveness of the resultant biocidal solution, and/or (iii) increase long term damage to a glass-lined reaction vessel in which the process is conducted. Hence, the term "substantially all of the time" is used herein to denote that such permissible departures are acceptable and are within the spirit and scope of this invention.

It is also important to understand the phrase "during all or substantially all of the time feeding in A) is occurring" as used herein. There are basically two sets of circumstances that are to be taken into consideration. The first case is where the process is being conducted as a batch process in making a given quantity or batch of the aqueous solution. Here the foregoing phrase refers to the period of time starting when contact between (a) and (b) is initiated by the feeding in A), and ending when the feeding in A) is terminated because the particular batch or quantity of aqueous solution with a pH in the range of about 7 to about 11, or with a pH in the preferred pH range of about 8 to about 10, has been formed. The second case is where the process is being conducted on a continuous process in which the aqueous solution is continuously being formed over a long period of time and is being removed either continuously or intermittently from the vessel or reaction zone in which it was formed. Here the foregoing phrase refers to the period of time starting when the feeds of (a) and (b) come into contact with each other in the vessel or reaction zone, and ending when the aqueous solution with a pH in the range of about 7 to about 11, or with a pH in the preferred pH range of about 8 to about 10, is removed from the vessel or reaction zone in which it was formed. In general there are two things that can be done with the aqueous solution with a pH in the range of about 7 to about 11, or at a pH in the preferred pH range of about 8 to about 10:

1) all or a part of the aqueous solution can be used as a biocide and thus such portion is consumed within a suitable period of time after its formation; and/or 2) the pH of all or a part of the aqueous solution can be raised to a pH of at least about 12, and preferably to a pH that is at least in the range of about 13 to about 13.5 within a suitable period of time after its formation, typically by including additional alkali metal base in such aqueous solution.

Use according to 1) would typically occur when periodically employing a small-scale production unit at the site of body of water requiring periodic sanitation. Further treatment according to 2) represents the more usual situation where the aqueous solution with a pH in the range of about 7 to about 11, or at a pH in the preferred pH range of about 8 to about 10 is used as the precursor of a finished concentrated liquid biocide composition suitable for storage and shipment to sites where ultimately it would be put to use and be consumed. The "suitable period of time" referred to in 1) and 2) above is a period of time before any significant (i.e., unacceptable) degradative change occurs in the aqueous solution with a pH within the pH range of about 7 to about 11, or within the preferred pH range of about 8 to about 10. The "suitable period of time" in turn will vary depending upon such factors as the pH and the temperature of the aqueous solution; typically the higher the pH between about 7 to about 11, and the lower the temperature of the solution, the longer can be this period of time. In any particular case where the duration of such suitable period of time has not been previously established, a few preliminary tests can be carried out to determine the time before significant degradative change occurs under particular pH and temperature conditions in any given aqueous solution with a pH in the range of about 7 to about 11, or with a pH in the preferred range of about 8 to about 10.

When coordinated separate feeds of (a) and (b) are both made into a reaction vessel, as distinguished from feeding (a) into (b), these separate feeds of both (a) and (b) into the reaction vessel need not be, but can be, continuous or intermittent, and/or concurrent or non-concurrent. Typically they are continuous or intermittent concurrent feeds. But they can be continuous or intermittent substantially concurrent feeds (i.e, feeds where part of the time one of (a) or (b) is not being fed while the other is being fed). No matter how these coordinated separate feeds of both (a) and (b) into the reaction vessel are carried out, the important thing is to ensure that such feeds are conducted so as to result in maintaining in the reaction vessel a pH to between about 7 and about 11, and preferably between about 8 and about 10, throughout or substantially throughout the time from the initiation of feeding until the pH of the resultant solution is raised to a pH of at least about 12, and preferably to a pH that is at least in the range of about 13 to about 13.5.

The use of bromine chloride and/or bromine and chlorine as the source of the active bromine enables flexibility in the design and operation of a facility employing the process technology of this invention and in addition, the most economical of these halogen source(s) can be selected from those available for use at such facility. For example, the feed of (a) employed can be (i) a feed of bromine chloride, (ii) separate and concurrent feeds of bromine and chlorine, (iii) bromine and chlorine fed successively or fed alternately three or more times, with either one being the initial feed, (iv) a feed of a mixture of bromine chloride and bromine, (v) separate and concurrent feeds of bromine chloride and bromine, (vi) bromine chloride and bromine fed successively or fed alternately three or more times, with either one being the initial feed, (vii) separate and concurrent feeds of bromine chloride, bromine and chlorine, and (viii) bromine chloride, bromine and chlorine fed in various sequences and/or subcombinations and/or combinations. Preferred feeds are single feed streams of either bromine chloride or a mixture of bromine chloride and bromine, or separate streams of bromine and chlorine, fed separately and concurrently, or fed separately and sequentially with either one being fed first. It has not escaped our attention that it may be possible to devise still other ways of accomplishing feeds of bromine chloride, bromine, and chlorine, and any such other way of feeding is within the contemplation and scope of this invention as it would be an equivalent to the feeds identified as (i) through (viii) in this paragraph.

No matter which of bromine chloride, bromine, and chlorine, is fed, and no matter in what sequences or combinations they are fed, both bromine atoms and chlorine atoms are to be fed, and the total amount of bromine atoms fed (whether fed as elemental bromine or as the bromine content of bromine chloride, or both) should not be appreciably lower than the total amount of chlorine atoms fed (whether fed as elemental chlorine or as the chlorine content of bromine chloride, or both), because the amount, if any, by which total chlorine atoms fed exceeds total bromine atoms fed, results in diminished biocidal effectiveness of the end product being produced. Thus in less preferred embodiments wherein the total number of chlorine atoms fed exceeds the total number of bromine atoms, such excess should not be more than about 5%. Preferably, the total amount of bromine atoms fed (whether fed as elemental bromine or as the bromine content of bromine chloride, or both) should be at least equal to, or up to about 2% in excess over the total amount of chlorine atoms fed (whether fed as elemental chlorine or as the chlorine content of bromine chloride, or both).

It is preferred to employ as (a), viz., the source of the active bromine in the above process, (i) bromine chloride, (ii) a mixture of bromine chloride and elemental bromine (e.g., up to about 0.35 mole of bromine per mole of bromine chloride), or (iii) elemental bromine and elemental chlorine (e.g., in the range of about 1 to about 1.7 mole of bromine per mole of chlorine). First of all, these are the simplest ways of providing bromine and chlorine atoms to the reaction mixture. Secondly, when fed in the amount of at least one atom of bromine per atom of chlorine, most of the bromine is made available as active bromine in the resulting aqueous biocidal compositions. In other words, the chlorine of the bromine chloride or of the chlorine fed is converted in the process to dissolved alkali metal chloride salt, thereby liberating the bromine from the bromine chloride as the active bromine content of the biocidal composition, and/or enabling the bromine fed as such to constitute the active bromine content of the biocidal composition. Thus the more expensive component of the bromine chloride and the more expensive element as between bromine and chlorine—viz., bromine—is effectively utilized in forming active bromine in the aqueous biocidal composition, and concurrently the less expensive component—the anionic chlorine in the bromine chloride or the chlorine fed as such—makes this beneficial result possible. For the same reasons, when bromine and chlorine are fed to the reaction solution, either (1) separately and concurrently, or (2) successively and optionally, alternately, their proportions should be such that about 1 to about 1.7 and preferably 1 to about 1.2 moles of bromine are fed per each mole of chlorine fed.

By utilizing the bromine and chlorine reagents of (a), especially bromine chloride or a mixture of bromine chloride and bromine or separate feeds of bromine and chlorine, with caustic in the stabilized bromine composition, higher levels of active halogen are achievable, compared to the levels obtained by the addition of sodium hypochlorite to sodium bromide. The process and the compositions formed also can have about twice the content of active bromine as the most concentrated solutions produced pursuant to the Goodenough, et al. patent. Moreover, even at the high levels of active bromine that preferably exist in the compositions of this invention, it has been found possible to provide biocidal compositions that maintain these high levels of active bromine for at least a two-month period, and that do not exhibit a visible or offensive vapor or odor during this period.

The processes of this invention can be conducted as a batch process or as a continuous process. A preferred way of conducting the processes as a continuous process comprises the following operations:

A) continuously feeding into mixing apparatus (a) bromine and chlorine atoms in the form of one or more of(i) bromine chloride, (ii) elemental bromine, and (iii) elemental chlorine, such that the numerical ratio of the total number of bromine atoms being fed to the total number of chlorine atoms being fed is in the range of about 0.7:1 to about 1.7:1, andpreferably in the range of about 1:1 to about 1.2:1, and (b) water containing sulfamate anion, preferably an aqueous solution of the sodium salt of sulfamic acid, the feeds of (a) and (b) being separate from each other;

B) continuously feeding into such mixing apparatus alkali metal base dissolved in water, this solution being fed as a part of feed (b), or as a separate concurrent continuous feed to such mixing apparatus, or both, the feeds of A) and B) being proportioned to produce an aqueous product solution having:
   i) a pH in the range of about 7 to about 11, and preferably in the range of about 8 to about 10,
   ii) a content of at least 50,000 ppm (wt/wt) of active bromine, i.e., at least 5 wt % of the solution being produced is active bromine, preferably at least about 100,000 ppm (wt/wt) of active bromine, and more preferably at least about 120,000 ppm of active bromine,
   iii) an atom ratio of nitrogen to active bromine originating from (a) and (b) of greater than 0.93, and preferably greater than 1, such as for example, in the range of about 1.1 to about 1.5, and
   iv) either no sulfate content or if sulfate is present, a sulfate content in an amount such that the molar ratio of sulfate to sulfamate in the solution being produced is less than 0.2, and preferably less than 0.05; and C) withdrawing said aqueous product solution from the mixing apparatus at a rate sufficient to enable the continuous feeding in A) and B) to be maintained.

The mixing apparatus can be a static mixer, or non-static mixing system such as a vessel equipped with a mechanical stirrer. If the mixing apparatus comprises a vessel equipped with a mechanical stirrer, the aqueous product solution can be withdrawn from the vessel either continuously or intermittently.

In conducting the above continuous process, it is preferred to produce (b), i.e., the water containing sulfamate anion, preferably an aqueous solution of the sodium salt of sulfamic acid at the same plant site. This solution can also contain excess alkali metal base such as sodium hydroxide. A highly efficient way of producing this solution is to continuously, but alternately, withdraw from at least one and then from at least one other of at least two reaction vessels, an aqueous solution of alkali metal salt of sulfamic acid at a rate that maintains the continuous feed of (b) in A), and during the time the solution is being withdrawn from at least one such reaction vessel, forming additional aqueous solution of alkali metal salt of sulfamic acid in at least one other reaction vessel from which solution is not then being withdrawn. In this way a supply of the aqueous solution of sulfamate is always available for use as the feed of (b) in A) above. All that is necessary, in the case of two vessels is to withdraw solution from filled vessel (I) until it is emptied while concurrently making in and filling vessel (II) with fresh solution, switch from emptied vessel (I) to filled vessel (II) and withdraw solution from vessel (II) until it is emptied while concurrently making in and filling vessel (I) with fresh solution, and repeating this procedure over and over again so as to continuously have available a supply of the solution for the continuous feed.

The above continuous process involves features of the continuous processes described in commonly-owned copending Application Ser. Nos. 09/442,025 and 09/663,948, referred to above and incorporated herein by reference.

A particularly preferred way of conducting the processes of this invention as a continuous process comprises the following operations:

1) continuously forming bromine chloride or a mixture of bromine chloride and bromine from separate feed streams of bromine and chlorine by maintaining said streams under automatic feed rate control whereby the streams are continuously proportioned to come together to form bromine chloride or a preselected mixture of bromine chloride and bromine;

2) continuously feeding into mixing apparatus (a) bromine chloride formed in 1), or a mixture of bromine chloride with elemental bromine formed in 1), and (b) water containing sulfamate anion, preferably an aqueous solution of the sodium salt of sulfamic acid, the feeds of (a) and (b) being separate from each other and under automatic feed rate control;

3) continuously feeding into such mixing apparatus alkali metal base dissolved in water, this solution being fed as a part of feed 2), or as a separate concurrent continuous feed to such mixing apparatus, or both, the feeds of2) and 3) being proportioned to produce a reaction mixture that becomes an aqueous product solution having:
   i) a pH in the range of about 7 to about 11, and preferably in the range of about 8 to about 10,
   ii) a content of at least 50,000 ppm (wt/wt) of active bromine, i.e., at least 5 wt % of the solution being produced is active bromine, preferably at least about 100,000 ppm (wt/wt) of active bromine, and more preferably at least about 120,000 ppm of active bromine,
   iii) an atom ratio of nitrogen to active bromine originating from (a) and (b) of greater than 0.93, and preferably greater than 1, such as for example, in the range of about 1.1 to about 1.5, and
   iv) either no sulfate content or if sulfate is present, a sulfate content in an amount such that the molar ratio of sulfate to sulfamate in the solution being produced is less than about 0.2, and preferably less than about 0.05;

4) keeping the temperature of the reaction mixture in a temperature range of about −10 to about 50° C. and preferably in the range of about 15 to about 25° C. by cooling such reaction mixture; and 5) withdrawing reaction mixture and/or said aqueous product solution from the mixing apparatus at a rate sufficient to enable the continuous feeding in 2) and 3) to be maintained.

In connection with 5) of this process it will be appreciated that although the reactions taking place in the reaction mixture are rapid, some reaction may still be occurring in the mixture if it is being continuously withdrawn from a static mixer with a short residence time. In such case what is being withdrawn in 5) is at least in part reaction mixture. On the other hand if the mixing apparatus is a large vessel equipped with a mechanical stirrer or a pumparound mixing loop, most if not all of what is withdrawn from the mixing apparatus will likely be aqueous product solution. In any event, the aqueous product solution recovered from the process can be, and preferably is, treated with enough water-soluble base such as sodium hydroxide to raise the pH to at least 12 and preferably to a pH that is at least in the range of about 13.0 to about 13.5.

As noted above, the mixing apparatus used in the above continuous process can be a static mixer, or non-static mixing system such as a vessel equipped with a mechanical stirrer or a pumparound mixing loop. If the mixing apparatus is a static mixer, the aqueous product solution will usually be continuously withdrawn therefrom. If the mixing apparatus comprises a vessel equipped with a mechanical stirrer or a pumparound mixing loop, the aqueous product solution can be withdrawn from the vessel either continuously or intermittently.

Preferably, the automatic feed rate controls in 1) and 2) are under nested cascade ratio flow control. If the solution of alkali metal base dissolved in water is fed as a separate concurrent continuous feed to the mixing apparatus, this feed stream should also be under automatic feed rate and pH control, and preferably under nested cascade ratio flow and pH control.

The above preferred continuous process involves features of the continuous processes described in commonly-owned copending application Ser. Nos. 09/451,344 and 09/663,788, referred to above and incorporated herein by reference.

Some of the continuous processes of these commonly-owned copending applications involve continuous feeds to the mixing apparatus. In addition, some of the continuous processes of these commonly-owned copending applications involve continuous formation of bromine chloride, or continuous contacting of bromine and chlorine to form bromine chloride, or continuous alternate withdrawal of an aqueous solution of alkali metal salt of sulfamic acid from at least one reaction vessel while another quantity of such solution is being formed in at least one other such vessel. In such embodiments the term "continuous" or "continuously" is not meant to exclude interrupted feeds or withdrawals. Generally, if such interruptions occur, they are of short duration and are such as not to materially affect the steady state operation of the overall process, and also are such as not to cause production of a significant quantity of off-specification concentrated product solution. An example of such a slight, non-adverse interruption may occur when switching the flow of aqueous solution of alkali metal salt of sulfamic acid from at least one reaction vessel to another such vessel, an operation which is referred to above as part of a "continuous" feed. As long as such switching operation does not disrupt the operation or result in the formation of a significant quantity of off-specification concentrated product solution, such interruption is acceptable and is within the spirit of the term "continuous". An exception exists where the term "continuous" does not allow for interruption, namely in any case where both continuous and non-continuous (e.g., "intermittent") operation in a given step or operation are both expressly referred to. An example of this exception is the embodiment where product is continuously withdrawn from above-referred-to vessel that is equipped with a mechanical stirrer or pumparound mixing loop. Such "continuous" withdrawal is not interrupted because in another embodiment expressly referred to herein, the withdrawal of the same product from the same vessel is specifically described as "intermittent". Thus both alternatives (continuous and non-continuous) are expressly referred to.

Reference is now made to the drawings, which are largely self-explanatory.
FIG. 1

In the plant flow diagram schematically depicted in FIG. 1, separate streams of bromine and chlorine are fed, preferably continuously, into stirred jacketed reactor 10. The contents of reactor 10 are typically maintained at a temperature in the range of about −30 to about 30° C. so that bromine chloride is produced, preferably continuously. The bromine chloride is transmitted continuously into mixing apparatus 20. Concurrently sulfamic acid, an aqueous solution of sodium hydroxide (e.g., 15–50 wt %), and water are charged into either jacketed reactor 30 or jacketed reactor 40, and the resultant mixture therein is agitated and maintained at about 10 to about 50° C. The sulfamic acid and the sodium hydroxide are proportioned to produce in the reactor an aqueous solution of sodium sulfamate having a pH which preferably is in the range of about 7.0 to about 14.0. The reactor 30 or 40 which is not then being used to prepare such aqueous sodium sulfamate solution, contains an identical aqueous solution previously made therein in the same manner. A stream of such aqueous sodium sulfamate solution is continuously withdrawn from reactor 30 or 40 (as the case may be) which contains the previously made solution, and this stream is continuously fed into mixing apparatus 20. The interaction between the bromine chloride and the sodium sulfamate solution tends to be exothermic. Therefore, it is desirable, particularly in large scale facilities, to cool the mixture as it is being formed. The effluent from mixing apparatus 20 is the reaction mixture having a pH in the range of about 7 to about 11, and preferably a pH in the range of about 8 to about 10, and thus the feeds from reactor 10 and from reactor 30 or 40 (whichever at the time is the source of the feed) are proportioned to produce a solution having such pH. Alternatively, additional caustic may be continuously added directly to vessel 20 to control the desired pH. This additional caustic can be controlled by measuring the pH of the exit stream of vessel 20 utilizing signals from pH probe 60 and by use of control valve 70 in the caustic supply line to vessel 20, control valve 70 being operated by a flow controller in response to the signals from pH probe 60. This precursor product solution is transferred from mixing apparatus 20 to another mixing vessel 50. If mixing apparatus 20 is a static mixer, the effluent from the static mixer is continuously transferred to mixing vessel 50. On the other hand, if mixing apparatus 20 is, say, a vessel equipped with a mechanical stirrer or a pumparound mixing loop, and such vessel is intermittently drained so that its contents oscillate between high and low contents of product solution, the transmission of the product solution from such mixing apparatus 20 to mixing vessel 50 is intermittent. Means (not shown) such as electrically-operated valves and associated electronics for sensing and signaling when to shut one valve while opening the other are included so that the continuous alternate flow of aqueous sodium sulfamate solution from one and then the other of reactors 30 and 40 to mixing apparatus 20 can be maintained on a continuous basis. An aqueous solution of alkali metal base such as 25 or 50 wt % aqueous sodium hydroxide is fed, preferably continuously, into mixing vessel 50 proportioned to raise the pH of the contents in mixing vessel to at least about 12, and preferably to a pH that is at least in the range of about 13.0 to about 13.5, to thereby form the concentrated stabilized aqueous biocidal formulation. The contents of mixing vessels 20 and 50 are preferably cooled so that the temperature of the contents does not exceed about 35° C., and preferably is a temperature below or at about room temperature, e.g., about 10 to about 25° C. The contents mixing vessel 50 can then be transferred to a storage tank (not shown) or equivalent container such as a railcar or tank truck.

Instead of the separate feeds depicted in FIG. 1 of sulfamic acid, a 10–50 wt % aqueous solution of sodium hydroxide, and water that alternate back and forth between one of reactors 30 and 40 while the other reactor is being drained, separate flows of the aqueous solution of sodium hydroxide and a preformed aqueous slurry of sulfamic can be fed alternately to these reactors. It may be expected that other variations and details in the depicted schematic plant flow diagram and/or in the mode of operation will now be readily apparent to those of ordinary skill in the art.

Automatic Process Flow Controls

Figure 2:
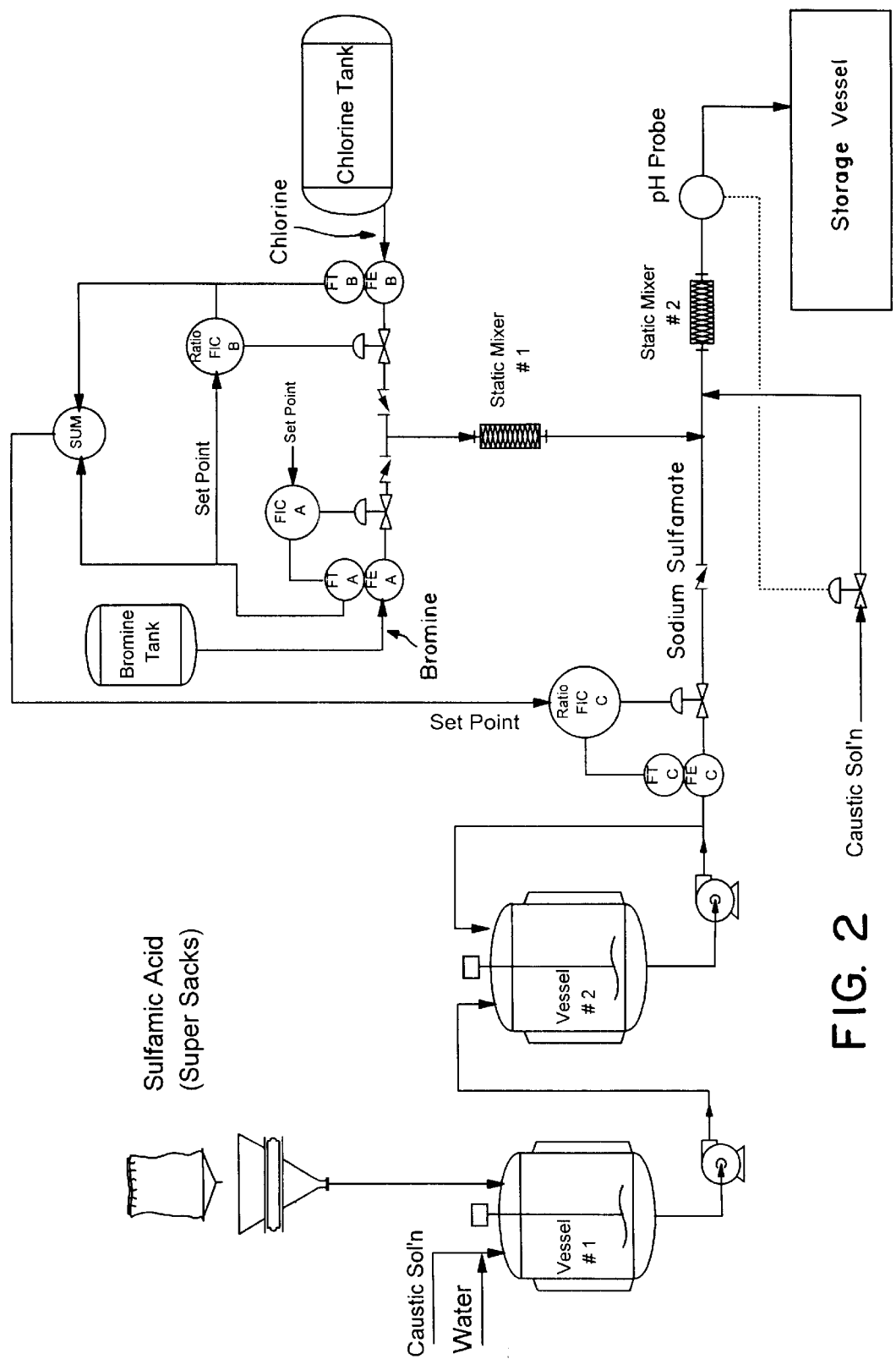
FIG. 2 is a schematic flow diagram of a plant layout in which an automatic flow control system is included.
Figure 3:
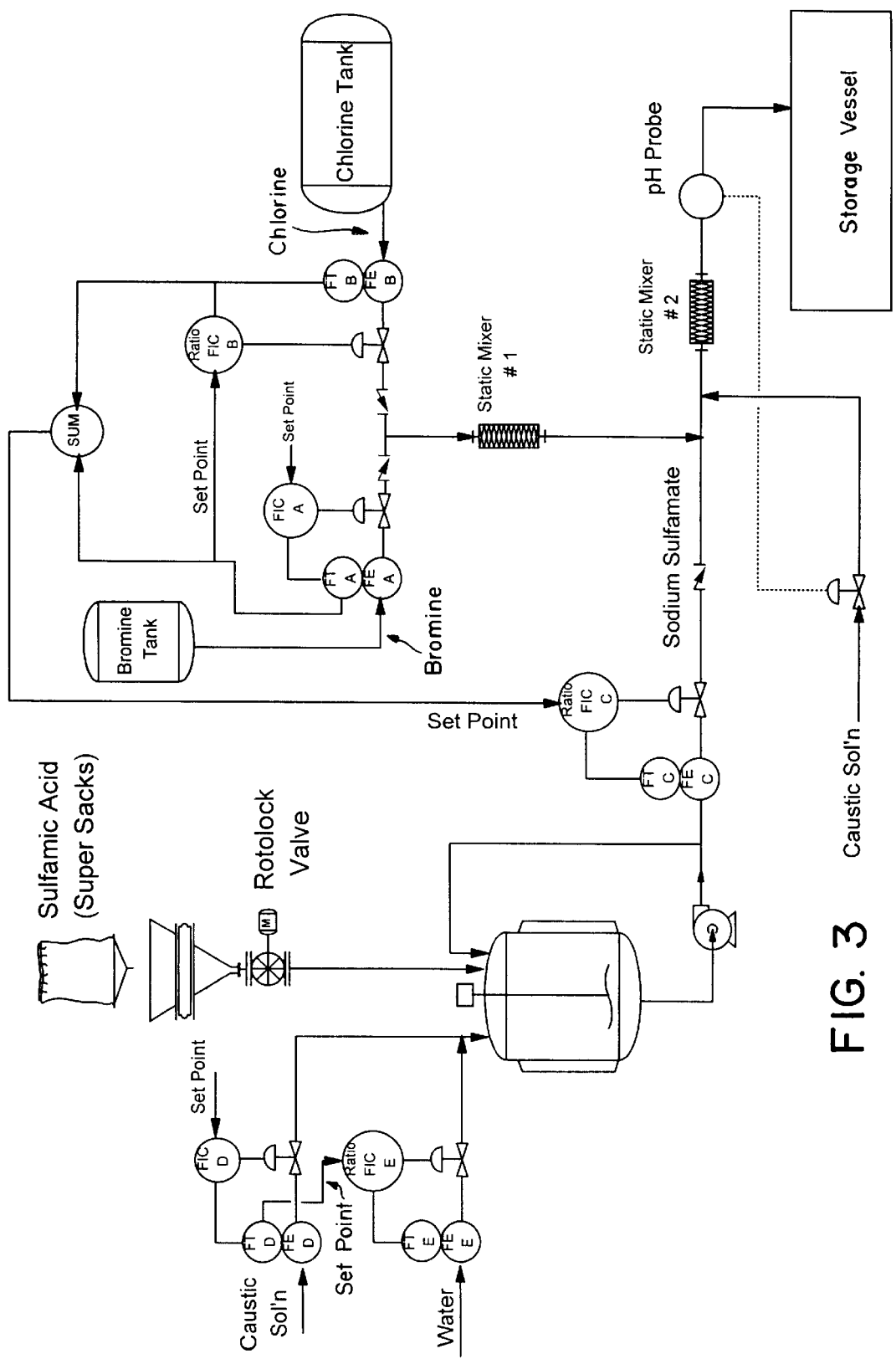
FIG. 3 is a schematic flow diagram of another plant layout in which an automatic flow control system is included.

In conducting a continuous process such as described above, the various continuous process embodiments are preferably carried out with automatic process flow controls now to be described. Exemplary flow diagrams involving such automatic process flow controls are schematically depicted in FIGS. 2 and 3. Both such flow diagrams utilize the same method to simultaneously feed bromine, chlorine, and sodium sulfamate. The difference between the two is that FIG. 2 requires two vessels. The first vessel is used to neutralize sulfamic acid to sodium sulfamate. The second vessel is used as a feed tank to continuously feed sodium sulfamate to the rest of the process. The flow diagram of FIG. 3 is a "one-pot" process using a single reactor vessel to continuously neutralize sulfamic acid and feed sodium sulfamate to the rest of the process. It is to be noted that FIGS. 2 and 3 illustrate exemplary flow diagrams involving automatic continuous process flow control in the steps of (a) forming bromine chloride or bromine chloride containing some excess elemental bromine from bromine and chlorine, and (b) forming an aqueous active-bromine-containing reaction solution having (1) a pH in the range of about 7 to about 11, and preferably a pH in the range of about 8 to about 10, (2) an active bromine content of at least about 50,000 ppm (wt/wt), and preferably at least about 100,000 ppm (wt/wt), (3) an atom ratio of nitrogen to active bromine originating from the bromine chloride or bromine chloride plus excess elemental bromine, and the sulfamate and base being used in the process up to this stage, and (4) either no sulfate content or if sulfate is present, an amount of sulfamate such that the molar ratio of sulfate to sulfamate in the solution is less than about 0.2, and preferably less than about 0.05. Similar, automatic flow control features can be applied if desired to the feed of base to this aqueous active-bromine-containing reaction solution to increase the pH to at least 12 or preferably to a pH that is at least in the range of about 13.0 to about 13.5.

The following process descriptions as regards FIGS. 2 and 3 utilize feedback process control logic. A description of the typical instrumentation elements is provided here to help better understand how this logic process works.

A feedback control loop (for flow control) consists of three elements: (1) a sensor device to measure flow, (2) a control valve to vary the flow, and (3) a flow controller to direct the control valve to open or close as necessary to maintain the desired flow. A feedback control loop (for pH control) consists of three elements: (1) a sensor device to measure pH, (2) a control valve to vary the flow, and (3) a flow controller to direct the control valve to open or close as necessary to maintain the desired pH.

Micro Motion coriolis mass flow meters have been utilized in past processes with demonstrated flow accuracy and are depicted in the following process descriptions. These instruments are available from Micro Motion, Inc. USA, 7070 Winchester Circle, Boulder, Colo. 80301. These particular instruments use coriolis technology to provide a direct mass flow rate indication (as opposed to a volumetric flow indication which must be converted to mass units and be corrected for temperature variation) and also contain a flow signal transmitter used to provide a feedback flow signal to a control system computer. The size specification of the mass meter depends on the magnitude of the desired flow, density/viscosity characteristics of the flowing liquid, and pressure drop inherent with the associated piping.

Typical automatic control valves are pneumatically actuated to raise/lower a stem in the valve body. A precisely machined and specifically contoured "trim" is attached to the stem and internally resides in the flow path within the valve body. The trim serves to vary the size of the flow orifice as the stem moves up and down. The trim size is specified to provide a particular flow range for a given pressure drop across the valve. The pneumatic actuation signal is typically provided from an I/P device used to convert an electronic signal from a controller (usually measured in milliamps with a 4–20 mA range) to a corresponding pneumatic signal (usually measured in gauge pressure with a 3–15 psig range). Air pressure is supplied to the I/P device which in turn supplies a precise pressure to actuate the valve. The I/P device is usually calibrated at 0–100% scale of a 4–20 mA electronic signal to correspond to a 3–15 psig pneumatic signal at 0–100% scale of the desired flow range (i.e., 4 mA=3 psig=0 flow, 20 mA=15 psig=100% flow). Depiction of the I/P devices have been omitted in the proposed flow diagrams of FIGS. 2 and 3 as they are universally assumed to be required. Size specification of the particular valve depends on the desired pressure drop across the valve, pipe size, and trim selection to provide the desired flow range. Control valves for ½ inch to 1 inch diameter process lines are typically available from Badger Meter, Inc. Industrial Division, 6116 East 15th St., Tulsa, Okla. 74158.

The controller is the heart of the control loop and is usually an electronic "black box" within the control system computer software. Most controllers are one of three types: Proportional (P), Proportional Integral (PI), or Proportional Integral Derivative (PID). The names reflect what type of response action will be taken to adjust the control signal. In depth descriptions of each type will not be provided here, as these are features known to those having ordinary skill in the art automatic process control. Most flow control loops use a PI controller due to the fast response nature of the flow measurement and control valve.

The overall feedback control loop functions as follows: A desired flow value (setpoint) is input to the controller. A sensor device measures the current flow (measured variable) and returns the current flow value to the controller. The controller calculates the error between the measured variable and the desired setpoint value. The controller then supplies a signal to the I/P and control valve to vary the position (manipulated variable) of the control valve for either increased or reduced flow to minimize the error between the actual and desired flow values. The determination of how fast or how much to vary the position of the control valve depends on the tuning parameters supplied to the controller for Proportional Integral response. The control loop is "tuned" by changing these parameters to achieve optimal response (error minimization) to process upsets or setpoint changes.

The processes of FIGS. 2 and 3 utilize nested cascade ratio flow control to continuously produce the concentrated liquid biocidal compositions. Cascade ratio control is based on feedback control loops. For this type of control, a primary material stream is controlled at a desired flow setpoint. The flow transmitter that provides feedback response to the controller, usually called the master controller, also sends a flow signal to a ratio controller. This signal becomes the setpoint for a second material stream flow controller and hence the term cascade. This controller, usually called the slave controller, provides a signal to a control valve controlling the flow of a second material stream. A flow element in the second stream measures the flow and returns a signal back to the ratio flow controller. The secondary controller calculates the error between the measured flow value and the remotely supplied setpoint. The secondary controller then provides a signal to vary the second control valve accordingly to maintain the secondary flow as a ratio of the primary flow.

The flow controllers are usually contained as individual block elements within the operating software of a process control computer system. A typical control system is a Foxboro I/A Distributed Control System (DCS).

FIG. 2

Reference will now be made specifically to FIG. 2. This Figure describes a flow control system in which the alkali metal sulfamate formed is sodium sulfamate using sodium hydroxide. However, the system is applicable to use of other alkali metal sulfamates formed using water-soluble bases other than sodium hydroxide. The control basis for the process of FIG. 2 is the nested cascade ratio flow control system employed to simultaneously control chlorine flow rate at a set ratio of a desired bromine flow rate. The combined total bromine/chlorine flow rate is then used to simultaneously control the sodium sulfamate flow rate at a desired ratio of the bromine/chlorine flow rate.

One of the vessels depicted is used to neutralize sulfamic acid to form sodium sulfamate. The desired water charge is added to such vessel. Solid sulfamic acid is charged from individual bags or supersacks to the same vessel with agitation to form an aqueous sulfamic acid slurry solution. An aqueous solution of 10–50% caustic (NaOH) is fed to the sulfamnic acid solution to form aqueous sodium sulfamate. The sodium sulfamate solution is then transferred via pump pressure to the second depicted vessel which is equipped with a pump around circulation loop. A feed stream from the circulation loop is used to feed sodium sulfamate to the remaining continuous portion of the process.

Liquid bromine is fed continuously from a pressurized bromine supply vessel. The bromine (primary stream) flows through a Micro Motion mass flow meter then through an automatic control valve. The desired bromine flow rate is input as a setpoint to the bromine flow controller (master controller). The flow controller then sends a signal to the bromine control valve to vary the flow to maintain the desired flow rate. A one-way check valve is installed downstream of the bromine control valve to prevent back flow into the bromine supply line.

Liquid chlorine is supplied continuously from a bulk supply vessel either by tank vapor pressure or augmented with nitrogen pressure. Chlorine (secondary stream) flows through a Micro Motion mass flow meter then through an automatic control valve. The flow rate signal from the primary bromine mass flow meter/transmitter is sent to the chlorine ratio flow controller as a remote setpoint. The chlorine ratio flow controller then sends a signal to the chlorine control valve to vary the chlorine flow as a ratio of the bromine flow rate. A one-way check valve is installed downstream of the chlorine control valve to prevent back flow into the chlorine supply line.

The bromine and chlorine lines are brought together into a multi-element static mixer, commonly available from Koch Engineering Company, Inc., P.O. Box 8127, Wichita, Kans. 67208. The static mixer functions to provide dynamic in-line mixing with minimal linear space and no moving parts.

The flow rate signals from both the bromine and chlorine mass flow meters/transmitters are output to the computer control system and are summed together to obtain an overall flow rate of both streams. The overall flow rate value is then sent to a second ratio flow controller as a remote set point for the sodium sulfamate stream. The sodium sulfamate stream is supplied from pump pressure from the pump around circulation loop on the second depicted vessel. This stream flows through a Micro Motion mass flow meter then through an automatic control valve. The flow rate signal from the sodium sulfamate mass flow meter/transmitter is sent to the ratio controller which sends a signal to the control valve to vary the sodium sulfamate flow rate as a ratio of the combined bromine/chlorine flow rate. A one-way check valve is installed downstream of the sodium sulfamate control valve to prevent back flow into the sodium sulfamate supply line.

The sodium sulfamate stream and the combined bromine/chlorine stream exiting the first static mixer are brought together into a second multi-element static mixer. Additional caustic may be added after the first static mixer, the rate of addition of which is controlled by a pH meter down steam of this second multi-element static mixer such that the pH of the liquid leaving the second multi-element static mixer is in the desired range. The exiting stream from this static mixer is the aqueous active-bromine-containing reaction solution having (1) a pH in the range of about 7 to about 11, and preferably a pH in the range of about 8 to about 10, (2) an active bromine content of at least about 50,000 ppm (wt/wt), and preferably at least about 100,000 ppm (wt/wt), (3) an atom ratio of nitrogen to active bromine originating from the bromine chloride or bromine chloride plus excess elemental bromine, and the sulfamate and base being used in the process up to this stage, and (4) either no sulfate content or if sulfate is present, an amount of sulfamate such that the molar ratio of sulfate to sulfamate in the solution is less than about 0.2, and preferably less than about 0.05. As noted above, it is preferred to raise the pH of this reaction solution to at least about 12 and preferably to a pH that is at least in the range of about 13.0 to about 13.5 by the inclusion Itherewith of additional base, such as sodium hydroxide, thereby forming the desired concentrated liquid biocidal composition, which is sent to a bulk product storage tank.

The advantage of the process flow system of FIG. 2 is that preparation of the sodium sulfamate solution can take place outside of the continuous portion of the process. The water, caustic, and sulfamic acid can be charged as normal batch operations with a large solution being prepared in advance and transferred to the sodium sulfamate feed vessel as required. Additionally the entire process can be controlled by entering a single set point for the desired bromine flow rate. All other material flow rates are obtained as internal remote setpoints. It should be noted that the magnitude of the desired flow ratios for the ratio controllers are typically configured within the individual controller as set parameters as opposed to user entered setpoint values.

FIG. 3

The process flows and control systems of FIG. 3 will now be considered. As is the case of FIG. 2, FIG. 3 is described with reference to a flow control system in which the alkali metal sulfamate is sodium sulfamate. However, the system is applicable to the use of any water-soluble alkali metal sulfamate formed using other water-soluble alkali metal bases.

The process of FIG. 3 eliminates the second vessel depicted in FIG. 2, the vessel that is used in FIG. 2 as a sodium sulfamate supply vessel. The overall system of FIG.

3 includes additional control elements for the single vessel of FIG. 3 to continuously neutralize sulfamic acid and to feed sodium sulfamate solution to the process. The continuous mixing process to feed bromine, chlorine, and sodium sulfamate remain as in FIG. 2.

In the process of FIG. 3, an aqueous solution of 10–50% caustic is fed to the reaction vessel depicted through a Micro Motion mass flow meter then through an automatic control valve. A desired caustic flow rate setpoint is entered into the caustic flow rate controller. The caustic flow controller then sends a signal to the control valve to suitably vary the caustic flow in order to maintain the desired flow rate. The flow rate signal from the caustic mass flow meter/transmitter is also sent as a remote setpoint to a water ratio flow controller.

Water is fed to the reaction vessel depicted through a Micro Motion mass flow meter then through an automatic control valve. The water ratio controller then sends a signal to the control valve to vary the water flow as a ratio of the caustic flow rate.

Solid sulfamic acid is charged to the depicted vessel at a flow rate consistent with the water/caustic flow to provide the necessary sulfamic acid/sodium sulfamate concentration within the vessel. A Rotolock valve is typically installed in the solids charge line to accomplish solids feeding at a set flow rate. This type of valve is a multi-vane rotary valve coupled to a direct current (DC) motor with a speed controller. The motor speed is adjusted to provide the desired solids feed rate (as determined from separate calibration for speed vs. flow rate). The Rotolock system can be further enhanced by instrumenting for automatic feedback control. This is usually accomplished by mounting the solids hopper feeding the Rotolock valve on weigh cells. For this setup, a desired solids feed rate is entered into a feed controller. The controller sends a signal to the motor to either speed up or slow down to achieve the desired flow rate. The solids flow rate is obtained by internal calculation of the loss-in-weight over time from the solids hopper. If the sulfamic acid charge system was instrumented for automatic control, the logical extension would be to send the solids flow rate signal to the caustic flow controller as a remote setpoint for the desired caustic flow. Since this step consists of a neutralization reaction, a certain amount of residence time is required for complete neutralization to sodium sulfamate. The available information indicates that the neutralization is mass transfer limited by the caustic feed rate and also by the cooling capacity of the reactor. This neutralization is somewhat exothermic and requires cooling to remove the generated heat. A pump around circulation loop is one way to provide sufficient residence time if the required sodium sulfamate flow rate for the rest of the process is not excessively large.

Bromine, chlorine, caustic, and sodium sulfamate are then fed, with flow control and pH control, identically as in the process of FIG. 2. Sodium sulfamate is fed continuously by taking a feed stream from the pump around circulation loop from the depicted reaction vessel and flowing through a mass flow meter and control valve. The desired flow rate is obtained as a remote setpoint to a ratio flow controller from the summation of the total bromine/chlorine feed rate.

The advantage to the process of FIG. 3 is the elimination of one process vessel. This elimination is offset, at least to some extent, by the expense of additional control elements required for feeding water, caustic, and sulfamic acid.

It will now be understood and appreciated that the automatic flow control systems described herein can be effectively utilized in process layouts other than those depicted in FIGS. 2 and 3. One example of one such other process layouts is described with reference to FIG. 1.

A general procedure for preparing the compositions of this invention on a batch basis using sulfamic acid involves, as a first step, forming a slurry of sulfamic acid in water. Typically the pH of this slurry is below 1 pH unit. Aqueous sodium hydroxide at a suitable concentration, e.g., 25% to 50% concentration, is then added until the solid is completely dissolved. Additional NaOH is added until the desired pH in the range of about 7 to about 11 is reached. The resultant solution thus corresponds to (b) above. The feed of (a) to (b) or the feed of each of (a) and (b) into a reaction vessel is then initiated at a rate to allow (a) to dissolve and react with the sulfamic acid without forming a pool of halogen on the bottom of the reactor, and without causing the pH of the resulting solution to materially depart from the range of about 7 to about 11 (or from the range of about 8 to about 10, if this preferred pH range is to be used). Sodium hydroxide (e.g., 25% to 50%) is co-fed to the reactor to maintain the pH in the range of about 7 to about 11, and preferably in the range of about 8 to about 10. It has been found that stable solutions containing over 26% active bromine (over 11.5% on an active chlorine basis) can be prepared by the process technology of this invention.

The source of sulfamate anions, such as an alkali metal sulfamate or water containing sulfamate anions, is preferably derived from sulfamic acid by neutralizing sulfamic acid with an amount of alkali metal base to totally neutralize the acid, or by mixing a water-soluble alkali metal salt of sulfamic acid with water. Use of, or formation of, an alkali metal salt of sulfamic acid is a desirable feature of this invention as these salts are more soluble in water than sulfamic acid itself, and thus the reaction mixture will contain a higher concentration of sulfamate anion than could be provided by use of sulfamic acid. It is possible, however, to feed sulfamic acid itself since the reaction mixture will contain water and alkali metal base, and thus sulfamate anion will be formed in the reaction mixture. The alkali metal salts used are usually lithium, sodium or potassium salts, as the rubidium and cesium salts, although usable, tend to be considerably more expensive. Of these salts, potassium sulfamate is preferred, and sodium sulfamate is most preferred. Similarly, when forming the alkali metal salts of sulfamic acid in conjunction with a process of this invention, the base used for forming such salts is an alkali metal base. While various alkali metal bases may be used (e.g., alkali metal carbonates such as sodium carbonate), the hydroxides (or oxides) of lithium, sodium, or potassium, are typically used, again for reasons of cost, and of these potassium hydroxide or oxide is preferred, and sodium hydroxide or oxide is more preferred. Most preferred is sodium hydroxide. Mixtures of alkali metal bases can be used, if desired.

The alkali metal base which can be co-fed to the reaction mixture to maintain the pH in the range of about 7 to 11 and preferably in the range of about 8 to about 10 during the feeding of (a), or (a) and (b), and to increase the pH of the solution after completion of such feed(s) to at least about 12 and preferably to a pH that is at least in the range of about 13 to about 13.5, are the alkali metal bases, including the preferences, referred to in the immediately preceding paragraph. While the base used during the feeding and the base used after the feeding can differ from each other, it is preferred to use the same alkali metal base, preferably potassium oxide or hydroxide, and more preferably sodium oxide or hydroxide, and most preferably sodium hydroxide, in both such operations.

The duration of the time period between (i) the completion of the feed of (a) into (b) or the completion of the separate feeds of (a) and (b) into the reaction vessel, and (ii)

the commencement of the addition of additional base to raise the pH of the product solution to at least about 12 and preferably to a pH that is at least in the range of about 13 to about 13.5, can vary within reasonable limits. The stability of active bromine species, although stabilized by sulfamate, increases with increasing pH. Thus if, after completion of the feed of (a) to (b) or the separate feeds of (a) and (b) into the reaction vessel, the product solution has a pH of 7, the pH should be increased with less delay than if the product solution after completion of such feed(s) has a pH of 11. Common sense should thus be exercised in how long, if at all, one waits after completing the feeding before increasing the pH by addition of the alkali metal base. Generally speaking, the shorter the period between feed completion and pH increase, the better. If by chance a product solution has been allowed to stand for longer than usual without yet increasing its pH, a sample of the product solution can be subjected to starch-iodine titration to determine the concentration of active bromine in the product solution. If the concentration is lower than desired, the product can be subjected to additional feeds to increase the concentration of active bromine in the solution to the desired level, followed by the step of increasing the pH of the product to at least about 12 and preferably to a pH that is at least in the range of about 13 to about 13.5.

In raising the pH of the product solution after the feeding, stepwise pH increases can be used if desired. However it is usually preferred to raise the pH to the intended final pH level in one step.

The process operations can be conducted under ordinary ambient conditions, i.e., initiating the reaction at room temperature and applying no heat during the reaction. However, it is preferred to cool the reaction mixture so that the temperature of the reaction mixture is kept below about 35° C. (e.g., in the range of about 25 to about 35° C.) throughout the entire reaction period. Indirect heat exchange with a cooling fluid such as refrigerated air or cooling water is a convenient way of maintaining the temperature the reaction temperature below about 35° C. However, other cooling methods can be used, if desired. Also temperatures below room temperature can be used, if desired.

A preferred way of conducting the process on a batch basis utilizes a glass-lined reactor equipped with a mechanical stirrer, a diptube for feeding bromine chloride subsurface to the liquid phase reactor contents, and a pumparound loop which includes a heat exchanger for cooling the contents flowing in the loop. The operating procedure is to charge water to the reactor, cool the water to below 25° C., add 50% aqueous NaOH solution to the reactor, cool the mixture to below about 25° C., and then add sulfamic acid while keeping the temperature below about 25° C. and agitating the reactor contents. Then separate co-feeds of bromine chloride and aqueous NaOH are initiated, the bromine chloride either containing the stoichiometric amount of bromine for BrCl, i.e., 69.3 wt % of $Br_2$, or a small excess of bromine of up to about 0.1 mole per mole of BrCl, such as about 0.034 mole of excess bromine per mole of BrCl. During this co-feeding the temperature of the reactor contents is kept at below about 20° C., the reaction contents are agitated, and the pH of the reactor contents is kept at about 9.0 to about 9.5. After these feeds have been completed, the resultant mixture is kept under these conditions for a ride period of about 15 minutes. Then 50% aqueous NaOH solution is added in quantity to bring the pH up to about 13.0–13.5. In conducting this operation the components are of preferably proportioned to produce a final product solution having the following characteristics: a pH of 13.1; an active bromine content of 15.5 wt % (i.e., 155,000 ppm (wt/wt) of active bromine); an atom ratio of nitrogen to active bromine originating from the sulfamic acid and the bromine chloride (plus the foregoing small excess of bromine therein, if such excess is present) charged to the reactor of 1.4: and a specific gravity>1.31 at 20° C.

The term "active bromine" of course refers to all bromine-containing species that are capable of biocidal activity. It is generally accepted in the art that all of the bromine in the +1 oxidation state is biocidally active and is thus included in the term "active bromine". As is well known in the art, bromine, bromine chloride, hypobromous acid, hypobromite ion, hydrogen tribromide, tribromide ion, and organo-N-brominated compounds have bromine in the +1 oxidation state. Thus these, as well as other such species to the extent they are present, constitute the active bromine content of the compositions of this invention. See, for example, U.S. Pat. No. 4,382,799 and U.S. Pat. No. 5,679,239. A well-established method in the art for determining the amount of active bromine in a solution is starch-iodine titration, which determines all of the active bromine in a sample, regardless of what species may constitute the active bromine. The usefulness and accuracy of the classical starch-iodine method for quantitative determination of bromine and many other oxidizing agents has long been known, as witness Chapter XIV of Willard-Furman, *Elementary Quantitative Analysis*, Third Edition, D. Van Nostrand Company, Inc., New York, Copyright 1933, 1935, 1940.

A typical starch-iodine titration to determine active bromine is carried out as follows: A magnetic stirrer and 50 milliliters of glacial acetic acid are placed in an iodine flask. The sample (usually about 0.2–0.5 g) for which the active bromine is to be determined is weighed and added to the flask containing the acetic acid. Water (50 milliliters) and aqueous potassium iodide (15% (wt/wt); 25 milliliters) are then added to the flask. The flask is stoppered using a water seal. The solution is then stirred for fifteen minutes, after which the flask is unstoppered and the stopper and seal area are rinsed into the flask with water. An automatic buret (Metrohm Limited) is filled with 0.1 normal sodium thiosulfate. The solution in the iodine flask is titrated with the 0.1 normal sodium thiosulfate; when a faint yellow color is observed, one milliliter of a 1 wt % starch solution in water is added, changing the color of the solution in the flask from faint yellow to blue. Titration with sodium thiosulfate continues until the blue color disappears. The amount of active bromine is calculated using the weight of the sample and the volume of sodium thiosulfate solution titrated. Thus, the amount of active bromine in a composition of this invention, regardless of actual chemical form, can be quantitatively determined.

A further embodiment of this invention is a concentrated liquid biocide composition comprising an aqueous solution containing a stable oxidizing bromine compound—i.e., a stabilized active bromine content—wherein the solution is free of detectable bromate, and the solution is either free of sulfate, or if sulfate is present, the molar ratio of sulfate to sulfamate in the concentrated liquid biocide composition as formed is less than about 0.2, and preferably less than about 0.05. Preferably such composition from its inception is free of detectable amounts of bromate, or in other words, the solution contains at all times from its inception less than 50 ppm of bromate. Such concentrated liquid biocide compositions can be produced by use of the process technology of this invention.

The active bromine content of concentrated liquid biocide compositions of this invention is typically at least about 50,000 ppm (wt/wt) (i.e., at least about 5 wt %), preferably at least about 100,000 ppm, and more preferably at least about 120,000 ppm, based on the total weight of the aqueous solution. Compositions containing in the range of about 145,000 to about 160,000 ppm (wt/wt) of active bromine can be prepared pursuant to this invention. Amounts above 160,000 ppm (wt/wt) are also within the scope of this invention. In other words, any concentration of the stabilized active bromine component(s) above about 160,000 ppm (wt/wt) that does not result in precipitate formation during storage or transportation of the concentrated solution under normal ambient temperature conditions constitutes a compositions of this invention. When used for microbiological control, the concentrated solutions of this invention are often mixed or diluted with, or introduced into, additional water, which typically is the water being treated for such microbiological control, so that the amount of active bromine in the water being treated for microbiological control is a microbiologically effective amount. The various compositions of the embodiments referred to in this paragraph preferably additionally contain dissolved chloride ion, most preferably in the presence of a stoichiometric excess of alkali metal cation, such as sodium or potassium cations. In contrast to certain other alkali metal salts, the alkali metal chloride salts have high solubilities in the aqueous medium of the concentrates of this invention, and thus pose no problem with respect to precipitate formation during storage, transportation, or use. In addition, the dissolved alkali metal chloride in the solutions of this invention minimize the extent to which oxygen or air becomes dissolved in the concentrated solutions.

A feature of this invention is that it is unnecessary to produce the concentrated aqueous biocide compositions of this invention by use of powerful oxidants such as ozone or peroxides, which are known to possess undesirable, and indeed, hazardous characteristics. Thus from the inception of their production, the compositions of this invention, even though unpurified, are and remain at all times free of adverse quantities of peroxides.

Still other embodiments of this invention include the following:

1) A concentrated biocidal composition containing sulfamate-stabilized bromonium ion, such composition (i) having a pH of at least 12 and preferably at least in the range of about 13 to about 13.5, (ii) from its inception not having had a pH below 6, (iii) from its inception not having had a pH below 7 for more than a total of about 1 hour, (iv) having either no sulfate content or a content of sulfate in which the molar ratio of sulfate to sulfamate in the composition is less than about 0.2, and preferably less than about 0.05, and (v) having at least about 5 wt % and preferably at least about 10 wt % of bromonium ion present, measured as $Br_2$, such wt % being based on the total weight of the composition.

2) A concentrated biocidal composition containing sulfamate-stabilized bromonium ion, such composition (i) containing in the range of about 5 wt % to up to at least about 16 wt % bromonium ion, measured as $Br_2$, such wt % being based upon the total weight of the composition, (ii) from its inception not having had a pH below 6, (iii) from its inception not having had a pH below 7 for more than a total of about 1 hour, (iv) having either no sulfate content or a content of sulfate in which the molar ratio of sulfate to sulfamate in the composition is less than about 0.2, and preferably less than about 0.05, and (v) from its inception, being free of detectable amounts of bromate ion.

3) A concentrated biocidal composition containing sulfamate-stabilized bromonium ion, such composition (i) containing at least about 5 wt % and preferably at least 10 wt % of bromonium ion, measured as $Br_2$, such wt % being based upon the total weight of the composition, (ii) having a pH greater than about 12, (iii) containing no detectable bromate ion, and (iv) having either no sulfate content or a content of sulfate in which the molar ratio of sulfate to sulfamate in the composition is less than about 0.2, and preferably less than about 0.05.

4) A concentrated biocidal composition containing stabilized oxidizing halogen obtained by the reaction of (a) BrCl, BrCl and $Br_2$, or $Br_2$ and $Cl_2$, and (b) $^\ominus SO_3NH_2$, such composition (i) having up to about 16 wt % bromonium ion, measured as $Br_2$, such wt % being based upon the total weight of the composition, (ii) having a pH of at least about 12 and preferably at least in the range of about 13 to about 13.5, and (iii) having either no sulfate content or a content of sulfate in which the molar ratio of sulfate to sulfamate in the composition is less than about 0.2, and preferably less than about 0.05.

5) A concentrated biocidal composition containing stabilized oxidizing halogen obtained by the reaction of (a) BrCl, BrCl and $Br_2$, or $Br_2$ and $Cl_2$, and (b) $^\ominus So_3NH_2$, such composition (i) having a pH of at least about 12 and preferably at least in the range of about 13 to about 13.5, and (iii) having either no sulfate content or a content of sulfate in which the molar ratio of sulfate to sulfamate in the composition is less than about 0.2, and preferably less than about 0.05.

6) A concentrated biocidal composition containing stabilized oxidizing halogen obtained by the reaction of (a) BrCl, BrCl and $Br_2$, or $Br_2$ and $Cl_2$, and (b) $^\ominus SO_3NH_2$, such composition having either no sulfate content or a content of sulfate in which the molar ratio of sulfate to sulfamate in the composition is less than about 0.2, and preferably less than about 0.05.

7) A concentrated biocidal composition containing at least about 10 wt % $^\ominus SO_3NH_2$ stabilized non-$BrO^\ominus$-oxidizing halogen, and having either no sulfate content or a content of sulfate in which the molar ratio of sulfate to sulfamate in the composition is less than about 0.2, and preferably less than about 0.05.

8) A concentrated biocidal composition containing sulfamate-stabilized on-$BrO^\ominus$-oxidizing halogen, such composition (i) having a pH of at least about 12, and preferably at least in the range of about 13 to about 13.5, and (ii) having either no sulfate content or a content of sulfate in which the molar ratio of sulfate to sulfamate in the composition is less than about 0.2, and preferably less than about 0.05.

9) An aqueous composition containing at least one sulfamate-stabilized oxidizing bromine species and having either no sulfate content or a content of sulfate in which the molar ratio of sulfate to sulfamate in the composition is less than about 0.2, and preferably less than about 0.05.

Preferably, but not necessarily, the composition of 1), 2), 3), 7), 8), and 9) immediately above are further characterized by comprising chloride ion in solution therein.

As is known in the art, bromate is a very undesirable component of aqueous systems. For example, U.S. Pat. No. 5,922,745 points out that in 1995 the United States Enviromnental Protection Agency published a paper identifying some health concerns relevant to bromate formation (G. Amy, et al., *Water Supply*, 1995, 13(1), 157), and that in the same year animal carcinogenesis was linked to the presence of low levels of bromate in drinking water (J. K. Falwell, and G. O'Neill, *Water Supply*, 1995, 13(1), 29). While some prior processing achieved reductions in the amount of bromate formed when producing stabilized aqueous bromine-containing biocides, there has remained a need for still further reductions in the amount of bromate present in such biocides. Pursuant to this invention, such further reductions have been made possible. It is believed that because of the pH conditions used in forming the compositions of this invention, the possibility of bromate formation caused by significant exposure of the composition to acidic conditions is virtually eliminated.

The analytical test procedure to be used for determining the concentration, if any, of bromate in the compositions of this invention is an ion chromatography procedure in which UV detection is employed. The equipment required for the conduct of this procedure is as follows:

a) Ion Chromatograph—Dionex DX-500 or equivalent, equipped with a UV detector and autosampler.

b) Data Acquisition and Analysis Device—VAX MULTICHROM or equivalent chromatography data collection and processing system.

c) Ion Chromatographic Column—Dionex lonPac AG9-HC guard column (p/n 051791) in-line with a Dionex lonPac AS9-HC column (p/n 051786).

d) Volumetric Pipettes—any standard type of suitable volume.

e) Autosampler Vials—1-mL with caps.

f) Volumetric Flasks—100-mL.

g) Syringe—5-cc plastic syringe.

h) Pretreatment Cartridge—OnGuard-H from Dionex (p/n 039596).

The chemicals required for use in the procedure are as follows: a) Water—Deionized water with a specific resistivity of 17.8 megohm-cm or greater.

b) Sodium Carbonate—"Baker Analyzed"® reagent grade or equivalent.

c) Sodium Bromate—"Baker Analyzed"® reagent grade or equivalent.

The conditions used for the ion chromatograph are as follows:

| | |
|---|---|
| Eluent: | 4.5 millimoles (mM) sodium carbonate |
| Flow-rate | 1.0 mL/minute |
| Injection volume | 50 microliter ($\mu$L) |
| Detector Range | UV at 210 nanometers (nm) |

The eluent is prepared by dissolving 0.4770 gram of the sodium carbonate in 1 liter of the deionized water. These are mixed well and the solution is filtered through a 0.2 IC compatible filter to degas the solution. The concentrated bromate standard solution is prepared by weighing 0.1180 gram±0.001 gram of the sodium bromate into a I00-mL volumetric flask and diluting to volume with deionized water. This produces a solution containing 1,000 micrograms per milliliter of bromate. This concentrated bromate solution should be made fresh at least weekly. The bromate working standard solution is prepared by pipetting 100-microliters of the concentrated bromate standard solution into a 100-mL volumetric flask and filling the flask to volume with deionized water. The solution is mixed well, and yields a standard concentration of 1.0 microgram per milliliter of bromate.

The detailed procedure used for conducting the analysis of an aqueous solution of this invention involves the following steps:

a) Weigh 0.25 gram of the sample solution into a 100-mL volumetric flask. Fill to volume with deionized water and mix well.

b) Flush the OnGuard cartridge with 2-mL of deionized water.

c) Load 5-mL of the sample into the syringe attached to the OnGuard cartridge, pass through at a flow rate of 2 milliliters per minute, and discard the first 3 milliliters. Collect into a 1-mL autosampler vial and cap for analysis.

d) Analyze the samples, making duplicate injections, using the Ion Chromatograph instrument conditions given above.

The calculations involved in the procedure are as follows:

a) Calibration Standard: For bromate, calculate a response factor as follows: $R=A/C$ where R is the response factor, A is the average area counts (2 injections), and C is concentration in micrograms per milliliter ($\mu$g/mL).

b) Samples: ppm bromate=$A/(R \times W)$ where A is the average area of sample peak (2 injections), R is the response factor, and W is the weight of the sample in grams.

Still other embodiments of this invention are storage-stable aqueous concentrated biocidal solution comprised of at least one active bromine species stabilized by the presence in the solution of sulfamate anions, such solution having a mole ratio of sulfate to sulfamate of less than about 0.2, and preferably less than about 0.05; a content of active bromine of at least about 50,000 ppm, preferably at least about 100,000 ppm, and most preferably at least 120,000 ppm of solution; an atom ratio of nitrogen from sulfamate to active bromine of greater than 0.93 and preferably greater than 1; and a pH of at least about 12, and preferably in the range of about 13 to about 13.5, wherein the biocidal effectiveness of said stable aqueous concentrated biocidal solution is at least equal to and preferably greater than the biocidal effectiveness of a solution made from the same ingredients in the same amounts and proportions and in the same way, except that the pH especially effective control of bacteria, algae, mollusks, and biomass.

It is contemplated on the basis of preliminary experimental indications, that an aqueous concentrated liquid biocide composition formed by a process ofthis invention should have greater biocidal effectiveness than a comparable composition made in the same way from the same materials in the same amounts with the exception that the pH is either below about 7 or above about 11 during all or substantially all of the time feeding in A) is occurring. Thus further embodiments of this invention include an aqueous concentrated liquid biocide composition formed by a process which comprises:

A) feeding (a) bromine atoms and chlorine atoms in the form of one or more of bromine chloride, elemental bromine and elemental chlorine into (b) water containing sulfamate anions, or feeding each of (a) and (b) into a reaction vessel, such that numerical ratio of the total number of bromine atoms fed to the total number of chlorine atoms fed is in the range of about 0.7:1 to about 1.7: 1, and preferably in the range of about 1:1 to about 1.2:1; and B) providing enough alkali metal base in the mixture being formed in A) to keep the pH of such mixture in the range of about 7 to about 11 during all or substantially all of the time feeding in A) is occurring, the amounts of (a) and (b) used being amounts that form an active-bromine-containing solution in which (i) the active bromine content is at least about 50,000 ppm (wt/wt), preferably at least about 100,000 ppm (wt/wt), and more preferably at least about 120,000 ppm (wt/wt) (ii) the atom ratio of nitrogen to active bromine originating from (a) and (b) is greater than about 0.93, and preferably greater than 1, and (iii) if any sulfate is present in the solution as formed, such sulfate content is such that the molar ratio of sulfate to sulfamate in the solution is less than about 0.2, and preferably less than about 0.05; and C) raising the pH of the active-bromine-containing solution so formed to at least about 12, and preferably at least to a pH in the range of about 13 to about 13.5, by mixing additional alkali metal base therewith;

The following examples are presented for purposes of illustration and not limitation. In these Examples, the reactions were performed in a 2-liter glass flask equipped with a pH probe, thermometer, mechanical stirrer and in Examples 1–4, a ⅛-inch OD diptube made from Teflon® polymer for feeding the bromine chloride, bromine or chlorine to the reaction mixture. In Example 5 two such diptubes were used, one for feeding bromine and the other for feeding chlorine. The flask was cooled during each reaction by use of either an external water bath or an external bath of water and ice. A peristaltic pump was used to feed the aqueous sodium hydroxide solution into the reaction mixture, and when bromine was used as the halogen feed, another peristaltic pump was used to effect the feed of the bromine. In all cases the pH was monitored with a an Orion Model 520A pH meter using a model 8272BN pH electrode (Orion Research Incorporated, The Schrafft Center, 529 Main Street, Boston, Mass. 02129. As is customary in the water treatment arts, the results are expressed as "total available chlorine" although in the practice of this invention the analysis actually represents the total available active bromine in the product formed.

EXAMPLE 1

A feed cylinder was charged with aqueous NaOH (313 mL; 401 g, 25 wt %). Water (333 g), sulfamic acid (232.2 g, 2.39 mol), and aqueous NaOH (653 g, 25 wt %) were charged to a 2-liter reactor equipped with a mechanical stirrer, which was cooled to 20° C. To this solution, $Br_2$ (139.4 g, 0.87 mol) was fed during 25 minutes while keeping the temperature in the reactor at or below 20° C. When the feeding of $Br_2$ was finished, the pH of the solution was 11.3. Next, the stirring rate was increased to 600 rpm, and $Cl_2$ (58.1 g, 0.82 mol) was added. During the $Cl_2$ addition, the temperature of the solution was kept at 12–18° C. When about 80% of the $Cl_2$ had been added (after 40 minutes), the pH of the solution was 7.28. At this point, feeding of some of the NaOH in the feed cylinder (25 mL, 31.3 g) was started. While continuing the feeds of NaOH and $Cl_2$, the pH of the solution was maintained between 6.9 and 7.1, and the temperature of the solution was maintained at 18–23° C. After about 10 more minutes, all of the $Cl_2$ had been added, and the NaOH feed was also stopped. The pH of the solution was 6.9, and was maintained at pH 6.9–7.3 and at about 20° C. for one hour; additional very small amounts of NaOH had to be added occasionally to keep the pH above 6.9. After the hour had passed, the remainder of the NaOH in the feed cylinder was added, bringing the solution pH to >12 while keeping the temperature of the reactor under 20° C. The solution was analyzed by starch-iodine titration, and was found to contain 6.49 wt % "available $Cl_2$" (i.e., 14.6 wt % available $Br_2$) in a yield of 98%. The detailed data on the feeds of $Cl_2$ and NaOH are presented in Table 1; the amounts shown are cumulative.

TABLE 1

| Time | Amount $Cl_2$ added | Amount NaOH added | pH | T |
| --- | --- | --- | --- | --- |
| 0 | start | — | 11.3 | 13° C. |
| 3 min. | 1.6 g | — | 11.25 | 12° C. |
| 9 min. | 8.7 g | — | 10.94 | 15° C. |
| 16 min. | 18.5 g | — | 10.50 | 18° C. |
| 22 min. | 25.3 g | — | 10.18 | 18° C. |
| 26 min. | 29.6 g | — | 9.94 | 18° C. |
| 29 min. | 32.7 g | — | 9.75 | — |
| 35 min. | 40.7 g | — | 8.99 | 18° C. |
| 38.5 min. | — | start | 7.86 | — |
| 41 min. | — | ~5 mL | 7.28 | — |
| 43 min. | 48.8 g | 10 mL | 7.3 | — |
| 46 min. | 52.3 g | 16 mL | 7.24 | — |
| 49 min. | 56.6 g | 23 mL | 7.16 | 23° C. |
| 50.5 min. | 57 g | 25 mL | 6.90 | — |

EXAMPLE 2

A feed cylinder was charged with aqueous NaOH (560 mL; 702 g, 25 wt %). Water (333 g), sulfamic acid (232.2 g, 2.39 mol), and aqueous NaOH (352 g, 25 wt %) were charged to a 2-liter reactor equipped with a mechanical stirrer; the pH of the resulting solution was 1.56. 45 Milliters of aqueous NaOH were added from the feed cylinder to the solution, bringing the pH to 12.14. To this solution, $Br_2$ (139.4 g, 0.87 mol) was fed during 30 minutes while cofeeding NaOH (135 mL) from the feed cylinder. During the cofeeding, the temperature in the reactor at 15–18° C. When the feeding of $Br_2$ was finished, the pH of the solution was 10.2. Next, the stirring rate was increased to 600 rpm, and $Cl_2$ (57.3 g, 0.81 mol) was cofed with NaOH, such that the pH of the solution was maintained between 8.06 and 9.78. During the $Cl_2$ addition, which lasted for 45 minutes, the temperature of the solution was kept at 16–20° C. At this point the addition of the NaOH solution was stopped for 15 minutes. The feed of the remainder of the NaOH in the feed cylinder was then restarted, bringing the solutionpH to >13 while keeping the temperature of the reactor under 20° C. The solution was analyzed by starch-iodine titration, and was found to contain 6.59 wt % "available $Cl_2$" (i.e., 14.8 wt % available $Br_2$). The detailed data on the feeds of $Br_2$, $Cl_2$ and NaOH are presented in Table 2; the amounts shown are cumulative.

TABLE 2

| Time | Amount halogen added | Amount NaOH added | pH | T |
| --- | --- | --- | --- | --- |
| 0 | | start | 1.56 | 15° C. |
| 9 min. | start $Br_2$ | 45 mL | 12.14 | 16° C. |
| 12 min. | 5 mL | — | 10.0 | 17° C. |
| 21 min. | 20 mL | 90 mL | 10.2 | 17° C. |
| 30 min. | 34 mL | 140 mL | 10.34 | 18° C. |
| 39 min. | 46 mL; stop $Br_2$ | 180 mL; stop | 10.2 | 15° C. |
| 59 min. | start $Cl_2$ | restart | 10.2 | 13° C. |
| 66 min. | 8.7 g | 190 mL; stop | 9.78 | 16° C. |
| 71 min. | 13.6 g | — | 9.12 | 16° C. |
| 72 min. | — | restart | 8.63 | — |
| 76 min. | 20.5 g | 200 mL | 8.36 | 17° C. |

TABLE 2-continued

| Time | Amount halogen added | Amount NaOH added | pH | T |
|---|---|---|---|---|
| 82 min. | 28.2 g | 212 mL | 8.39 | 18° C. |
| 91 min. | 40.1 g | 235 mL | 8.23 | 17° C. |
| 95 min. | 45.7 g | 248 mL | 8.15 | 18° C. |
| 100 min. | 52.0 g | 260 mL | 8.09 | 20° C. |
| 104 min. | 57 g; stop | 270 mL; stop | 8.08 | 17° C. |
| 120 min. | — | restart | 8.06 | 18° C. |
| 122 min. | — | 275 mL | 9.02 | |
| 128 min. | — | 360 mL | 10.7 | 17° C. |
| 135 min. | — | 560 mL | — | 20° C. |

EXAMPLE 3

A feed cylinder was charged with aqueous NaOH (548 mL; 685.3 g, 25 wt %). Water (333 g), sulfamic acid (232.2 g, 2.39 mol), and aqueous NaOH (368.7 g, 25 wt %) were charged to a 2-liter reactor equipped with a mechanical stirrer; the pH of the resulting solution was 1.8. 30 Milliliters of aqueous NaOH from the feed cylinder were added to the solution, bringing the pH to 11.02. To this solution, $Br_2$ (139.8 g, 0.87 mol) was fed during 24 minutes while cofeeding NaOH (128 mL) from the feed cylinder. During the cofeeding, the temperature in the reactor at 14–17° C. When the feeding of $Br_2$ was finished, the pH of the solution was 9.69. Next, the stirring rate was increased to 670 rpm, and $Cl_2$ (57.37 g, 0.81 mol) was cofed with NaOH, such that the pH of the solution was maintained between 9.51 and 9.61. During the $Cl_2$ addition, which lasted for 44 minutes, the temperature of the solution was kept at 15–19° C. The feed of the remainder of the NaOH in the feed cylinder continued, bringing the solution pH to 13.2 while keeping the temperature of the reactor under 20° C. The solution was analyzed by starch-iodine titration, and was found to contain 6.47 wt % "available $Cl_2$" (14.6 wt % available $Br_2$). The detailed data on the feeds of $Br_2$, $Cl_2$ and NaOH are presented in Table 3; the amounts shown are cumulative.

TABLE 3

| Time | Amount halogen added | Amount NaOH added | pH | T |
|---|---|---|---|---|
| 0 | — | start | 11.02 | 18° C. |
| 2 min. | start $Br_2$ | 8 mL | 12.5 | 15° C. |
| 4 min. | 4 mL | 14 mL | 10.7 | 14° C. |
| 11 min. | 8.5 mL | 48 mL | 9.69 | 14° C. |
| | 21.5 mL | 118 mL | 9.69 | 17° C. |
| 26 min. | 46.5 mL; stop $Br_2$ | 128 mL; stop | — | — |
| 28 min. | start $Cl_2$ | restart | — | — |
| 30 min. | 3.5 g | 133 mL | 9.60 | 19° C. |
| 40 min. | 15.5 g | 158 mL | 9.63 | 16° C. |
| 45 min. | 24.9 g | 178 mL | 9.52 | 15° C. |
| 49 min. | 30.3 g | 188 mL | 9.52 | 15° C. |
| 56 min. | 38.9 g | 208 mL | 9.52 | 16° C. |
| 65 min. | 49.3 g | 230 mL | 9.52 | 19° C. |
| 72 min. | 57 g; stop | 248 mL; stop | 9.51 | 18° C. |
| 92 min. | — | restart | 9.50 | 18° C. |
| 94 min. | — | 268 mL | 9.90 | 18° C. |
| 97 min. | — | 293 mL | 10.41 | 18° C. |
| 118 min. | — | 518 mL | 13.2 | — |

EXAMPLE 4

A feed cylinder was charged with aqueous NaOH (390 mL; 493.4 g, 25 wt %). Water (333 g), sulfamic acid (232.2 g, 2.39 mol), and aqueous NaOH (560.6 g, 25 wt %) were charged to a 2-liter reactor equipped with a mechanical stirrer. To this solution, $Cl_2$ (57.15 g, 0.80 mol) was fed during 44 minutes, with the stirring rate at 670 rpm. The temperature of the solution was kept at 14–18° C. When the feeding of $Cl_2$ was finished, the pH of the solution was 9.64. Next, $Br_2$ (139.6 g, 0.87 mol) was cofed with some of the NaOH from the feed cylinder, such that the pH of the solution was maintained between 7.76 and 9.16. During the $Br_2$ addition, which lasted for 29 minutes, the temperature of the solution was kept at 15–19° C. At the end of the $Br_2$ addition, the feed of NaOH was also stopped. After 20 minutes, the remainder of the NaOH in the feed cylinder was added to the solution, while keeping the temperature of the reactor under 22° C. This resulted in a solution pH of 13.1. The solution was analyzed by starch-iodine titration, and was found to contain 6.37 wt % available $Cl_2$ (14.3 wt % available $Br_2$). The detailed data on the feeds of $Br_2$, $Cl_2$ and NaOH are presented in Table 4; the amounts shown are cumulative.

TABLE 4

| Time | Amount halogen added | Amount NaOH added | pH | T |
|---|---|---|---|---|
| 0 | start $Cl_2$ | — | — | 15° C. |
| 4 min. | 9.1 g | — | 13.41 | 18° C. |
| 18 min. | 23.3 g | — | 13.36 | 16° C. |
| 25 min. | 33.0 g | — | 12.68 | 17° C. |
| 27 min. | 35.7 g | — | 11.50 | 17° C. |
| 33 min. | 43.2 g | — | 10.53 | — |
| 38 min. | 49.9 g | — | 10.12 | 15° C. |
| 42 min. | 54.7 g | — | 9.82 | 14° C. |
| 44 min. | 57 g; stop $Cl_2$ | — | 9.64 | 15° C. |
| 47 min. | start $Br_2$ | — | 9.16 | 15° C. |
| 49 min. | 2 mL | start | 8.70 | — |
| 51 min. | 7 mL | ~20 mL | 8.53 | — |
| 55 min. | 14 mL | 33 mL | 8.62 | 18° C. |
| 60 min. | 21 mL | 45 mL | 8.61 | 17° C. |
| 64 min. | 28 mL | 61 mL | 8.41 | 15° C. |
| 67 min. | 32 mL | 72 mL | 8.27 | 15° C. |
| 71 min. | 37 mL | 85 mL | 8.19 | 16° C. |
| 73 min. | 42 mL | — | — | 18° C. |
| 76 min. | 46 mL; stop $Br_2$ | 105 mL; stop | 7.76 | — |
| 88 min. | — | — | 7.63 | 19° C. |
| 96 min. | — | restart | 7.58 | 19° C. |
| 97 min. | — | 108 mL | 8.6 | 20° C. |
| 99 min. | — | 122 mL | 9.4 | 19° C. |
| 123 min. | — | 390 mL | 13.1 | 22° C. |

EXAMPLE 5

As noted above, the apparatus was the same as in the other Examples except that two ⅛-inch Teflon® polymer diptubes were used, one for feeding bromine and the other for feeding chlorine. A feed cylinder was charged with aqueous NaOH (540 mL; 684 g, 25 wt %). Water (333 g), sulfamic acid (232.2 g, 2.39 mol), and aqueous NaOH (370 g, 25 wt %) were charged to the 2-liter reactor; the pH of the resulting solution was 1.95. 30 Milliliters of aqueous NaOH from the feed cylinder were added to the solution, bringing the pH to 12.4. To this solution, $Br_2$ (139.2 g, 0.87 mol) and $Cl_2$ (57 g, 0.80 mol) were fed concurrently during almost all of an 81-minute period while also feeding NaOH (290 mL) from the feed cylinder. During this concurrent feeding of $Br_2$, $Cl_2$, and NaOH, the temperature in the reactor was kept at 16–19° C. When the feeding of $Br_2$ and $Cl_2$ was finished, the feed of the NaOH was stopped, and the pH of the solution was 10.49. The reaction mixture was kept at 17° C. for a dwell or ride time of 19 minutes during which the pH dropped to 10.46. Then the feed of the NaOH was restarted and continued until all of the NaOH in the feed cylinder had been added, bringing the solution pH to greater than 10.7 while keeping the temperature of the reactor under 20° C. The solution was analyzed by starch-iodine titration, and was found to contain 6.28 wt % "available $Cl_2$" (14.1 wt % available $Br_2$). The detailed data on the feeds of $Br_2$, $Cl_2$ and NaOH are presented in Table 5; the amounts shown are cumulative.

TABLE 5

| Time, min. | $Br_2$ added, mL | $Cl_2$ added, g | NaOH added, mL | pH | T, °C. |
|---|---|---|---|---|---|
| 0 | 0 | 0 | 0 | 1.95 | — |
| 7 | 0 | 0 | 30 | 12.4 | — |
| 11 | 0 start | 0 start | start | — | — |
| 13 | — | — | — | 10.7 | — |
| 14 | — | — | — | 10.47 | — |
| 18 | 3 | 5.1 | 50 | 10.47 | 16 |
| 30 | 10 | 15.1 | 100 | 10.49 | 17 |
| 37 | 13 | 21.6 | 130 | 10.47 | 19 |
| 45 | 17 | 28.6 | 160 | 10.47 | 18 |
| 55 | 22.5 | 35.14 | 200 | 10.49 | 18 |
| 66 | 29 | 44.1 | 250 | 10.5 | — |
| 84 | 39 | 57 stop | 320 | 10.5 | 17 |
| 92 | 43 stop | — | 330 stop | 10.49 | 17 |
| 111 | — | — | restart | 10.46 | — |
| 114 | — | — | 355 | 10.7 | — |
| 135 | — | — | 540 | — | — |

To employ the compositions of this invention for disinfecting a surface such as a sink, a floor, a table top, a counter top, a bath tub, a stall shower, a toilet bowl, an air filter, cooling surfaces of an air conditioner, or the like, the composition, with or without further dilution with water, can be applied to such surface in any appropriate manner. For example, the composition can be applied to the surface by pouring or spraying the liquid biocide composition onto said surface either in its original concentrated state or after dilution with water. Alternatively, the liquid biocide composition, with or without further dilution with water, can be applied by means of an applicator, such as for example a cloth, sponge, paper towel, or mop. If the concentrate is diluted with water prior to or during use, the amount of dilution should of course provide a diluted solution having the requisite microbiocidal effectiveness. Generally speaking, the concentration of the diluted concentrate should be at least about 2 milligrams per liter of "active chlorine" or "total available chlorine". Because of prior custom and usage in the art, amounts of biocidal agents are often expressed in terms of "active chlorine" or "total available chlorine" even though the halogen may in fact be bromine. To convert a concentration of active bromine into "active chlorine" or "total available chlorine", the concentration of active bromine is multiplied by 0.444. Depending upon the strength of a particular concentrate of this invention (i.e., its concentration of active bromine (typically expressed in the art as active $Cl_2$ or available $Cl_2$), and the range of uses for which the composition is recommended, suitable instructions in terms readily understandable by the consumer can and should be placed on the containers or on the labels affixed to the containers in which the particular concentrate of this invention is sold or distributed for sale.

The method of sanitizing a body of water using a concentrated liquid biocide composition of this invention comprises introducing such composition, with or without prior dilution with water, into the body of water. A variety of methods may be used to introduce the concentrated liquid biocide composition to the body of water to be sanitized. The concentrated liquid biocide composition may be added directly to the body of water, either all at once or slowly over time, for example via a pump or feeder. In systems in which the water is circulated through an apparatus, the concentrated liquid biocide composition may be added to this apparatus.

The addition of the concentrated liquid biocide composition to the body of water to be sanitized preferably yields a concentration of biocide in the body of water such that in the range of from about 2 to about 10 milligrams per liter of "active chlorine" or "total available chlorine", expressed as $Cl_2$, is present in the body of water. In a preferred embodiment, the concentrated liquid biocide composition is introduced into the body of water as required, such that in the range of from about 2 to about 10 milligrams per liter of "active chlorine" or "total available chlorine", expressed as $Cl_2$, is maintained within the body of water. A more preferred amount of "total available chlorine", expressed as $Cl_2$, in the body of water is from about 2 to about 5 milligrams per liter. These concentrations of total available halogen, expressed as $Cl_2$, are known in the art to be sufficient for sanitizing a body of water and for maintaining sanitization of a body of water.

PART TWO

It will be recalled that one of the embodiments of this invention is a process of producing a liquid biocide composition wherein the pH of the reaction mixture is controlled 56 in at least three stages. The process of this embodiment comprises:

I) bringing together in any feasible manner to form a reaction mixture (a) bromine atoms and chlorine atoms in the form of one or more of (i) bromine chloride, (ii) elemental bromine, and (iii) elemental chlorine, (b) a source of sulfamate anions, preferably an alkali metal sulfamate, and more preferably sodium sulfamate, (c) alkali metal base, preferably a sodium base, and most preferably sodium hydroxide and/or sodium oxide, and (d) water, such that (1) the numerical ratio of bromine atoms to chlorine atoms brought into the mixture is in the range of about 0.7:1 to about 1.7:1, and preferably in the range of about 1:1 to about 1.2:1, and (2) the atom ratio of nitrogen to active bromine originating from (a) and (b) is greater than about 0.93, and preferably greater than about 1; to form an active-bromine-containing reaction product mixture that has, initially, a pH over 11, preferably at least about 12, and more preferably at least about 13;

II) providing before and/or during the conduct of I) an amount of alkali metal base in relation to the total amount of acid (HBr and/or HCl) co-product(s) to be formed in the reaction, that results in the pH of such reaction product mixture decreasing by at least 1 pH unit during the conduct of I), to a pH in the range of about 7 to about 11, and preferably to a pH in the range of about 8 to about 10;

III) keeping the reaction mixture at a pH in the range of about 7 to about 11, and preferably at a pH in the range of about 8 to about 10 for a period of time that increases the microbiocidal effectiveness of the concentrated liquid biocide composition being formed; and then IV) raising the pH of the resultant active-bromine-containing reaction product mixture to at least about 12, and preferably to a pH that is at least in the range of about 13 to about 13.5, by mixing additional alkali metal base therewith.

A preferred way of conducting the above process comprises:

I) feeding (a) bromine atoms and chlorine atoms in the form of one or more of (i) bromine chloride, (ii) elemental bromine, and (iii) elemental chlorine, into (b) an aqueous solution of sulfamate anions and alkali metal base, or feeding each of (a) and (b) into a reaction vessel, such that (1) the numerical ratio of the total number of bromine atoms fed to chlorine atoms fed is in the range of about 0.7:1 to about 1.7:1, and preferably in the range of about 1:1 to about 1.2:1, and (2) the atom ratio of nitrogen to active bromine originating from (a) and (b) is greater than about 0.93, and preferably greater than about 1; to form an active-bromine-containing reaction product mixture that has, initially, a pH over 11, preferably at least about 12, and more preferably at least about 13;

II) providing before and/or during the feeding in I) an amount of alkali metal base in 10 relation to the total amount of acid (HBr and/or HCl) co-product(s) to be formed in the reaction, that results in the pH of such reaction product mixture decreasing by at least 1 pH unit during the feeding in I), to a pH in the range of about 7 to about 11, and preferably to a pH in the range of about 8 to about 10;

III) keeping the reaction mixture at a pH in the range of about 7 to about 11, and preferably at a pH in the range of about 8 to about 10 for a period of time that increases the microbiocidal effectiveness of the concentrated liquid biocide composition being formed; and then IV) raising the pH of the resultant active-bromine-containing reaction product mixture to at least about 12, and preferably to a pH that is at least in the range of about 13 to about 13.5, by mixing additional alkali metal base therewith.

Sections I) and II) above involve in part mixing (a) and (b) in any suitable manner, such as by feeding (a) into (b) in the presence of an alkaline aqueous medium in which the pH is over 11, or by introducing separate feeds of (a) and (b) into a reaction vessel so these feeds come together in the presence of an alkaline aqueous medium in which the pH is over 11. However, other ways of bringing (a) and (b) into contact with each other in the presence of an alkaline aqueous medium in which the pH is over 11 can be used, such as concurrent separate feeds of (a) and (b), and of another separate feed of a solution of alkali metal base, into a reaction vessel, or separate concurrent feeds of (a) and of a separate feed of a water solution containing sulfamate anions and an alkali metal base into a reaction vessel. In short, any way of bringing (a), (b), water, and alkali metal base together can be used except that it is not desirable to feed (b), water, and alkali metal base into (a).

The amounts of (a) and (b) used in I) are preferably, but not necessarily, amounts that form an active-bromine-containing reaction product mixture in which (i) the active bromine content is at least about 50,000 ppm (wt/wt) (i.e., at least 5 wt % of the total weight of such product mixture), more preferably at least about 100,000 ppm (wt/wt), and still more preferably at least about 120,000 ppm (wt/wt).

As specified in Section II) above, an amount of alkali metal base is provided before and/or during the feeding in I) relative to the amount of acid being formed as co-product(s) in the reaction mixture to result in the pH of the reaction mixture decreasing by at least 1 pH unit during the feeding in I) to a pH in the range of 7 to about 11, and preferably in the range of about 8 to about 10. It is generally understood that among the reactions taking place during the mixing of (a) and (b) when the base is a sodium base are the following reactions:

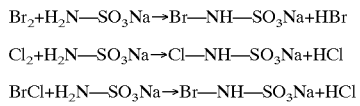

Thus halogen acid (e.g., HBr and/or HCl) is generated in the reaction mixture as the reaction is taking place. Pursuant to II), the amount of alkali metal base used is proportioned in to relation to the amount of acid being formed and to be formed during the reaction(s) so that the specified decrease in pH occurs. There is no need to attempt the identify the particular acid(s) formed in the reaction mixture; use of the stoichiometry of acid formation such as by use of equations such as those given above suffice for calculating the amount of base to be used to result in the pH reduction to be achieved. And if necessary pH measurements can be used to ensure that the decrease to the selected pH of over 1 pH unit to a pH within the range of about 7 to about 11 (and preferably within the range of about 8 to about 10) has in fact been achieved. While this decrease is a decrease of at least 1 pH unit, preferably it is a decrease of at least 2 pH units, and more preferably a decrease of at least 3 pH units, but whatever the extent of the decrease, the pH of the reaction mixture should not decrease below about 7, although one or more decreases below a pH of about 7 are permissible and within the scope of this invention provided the conduct of the process or the characteristics and properties of the end product are not adversely affected in any significant way. Decrease(s) in pH below about 7, if any, should thus be minimized in duration and magnitude to the greatest extent possible under any given set of circumstances.

If the process is conducted in a glass-lined reaction vessel, which is a preferred way to conduct the process, degradation of the glass can be minimized by minimizing the time during which the pH is above 11, or above 12, and especially at 13 or above, by initiating the decrease in pH as soon as or very soon after the mixture with the initial pH above 11, 12 or 13 has been formed in I).

During stage I) an active-bromine-containing reaction mixture is formed which is believed to contain, among other things, (1) molecular species containing bromine and nitrogen atoms, and (2) molecular species containing chlorine and nitrogen atoms. Typically approximately 20 mole % of the available halogen in this reaction mixture is apparently made up of the molecular species containing chlorine and nitrogen. Available evidence further indicates, quite convincingly, that the molecular species containing bromine and nitrogen atoms is/are more effective in microbiocidal effect than the molecular species containing chlorine and nitrogen atoms.

Pursuant to Section II) of this "Three Stage Process" the pH of the active-bromine-containing reaction mixture initially formed in Section I) is reduced by at least 1 pH unit and preferably by at least 2 pH units and more preferably by at least 3 pH units, to a pH in the range of about 7 to about 11, and preferably to a pH in the range of about 7 to about 10. This reduction in pH, caused by suitably proportioning the amount of base used, can be (i) a progressive, continuous transition from the initial high pH to the selected pH in the range of about 7 to about 11, or (ii) a stepwise transition from the initial high pH to the selected pH in the range of about 7 to about 11, or (iii) a combination of(i) and (ii), depending on the feeding techniques used. Alternatively, and less desirably, the pH can be reduced in whole or in part by addition to the reaction mixture of HCl or preferably, HBr.

In Section III) the reaction mixture is kept at a pH in the range of about 7 to about 11, and preferably at a pH in the range of about 7 to about 10 for a period of time. This period of time typically is a period of time after the feeding has been terminated, but can also include time during the feeding when the pH has decreased to a pH of 11 and remains at a pH of 11 down to about 7. The minimum length of this time period is not susceptible to precise numerical definition, as this depends on such factors as the actual pH of the reaction mixture, and apparently on other factors such as temperature. As a rule of thumb, the lower the pH value within the range selected, the shorter can be this time period, and the higher the pH value within the range selected, the longer should be this time period. But, the fact that the pH does not have to stay at one pH within these pH ranges but instead can vary within the ranges during this period of time, furtherpoints up the futility of trying to define the minimum time period the reaction mixture is to held within one or both of the foregoing ranges. What can be said, however, is that the length of this time period should be such as to result in the production of a concentrated liquid biocide composition having increased microbiocidal effectiveness. Without being bound by theory, it is believed that at the pH ranges of about 7 to about 11, some kind of halogen displacement or replacement takes place whereby the atomic chlorine of the molecular species containing chlorine and nitrogen atoms in the reaction mixture is displaced or removed, and replaced by atomic bromine from one or more sources within the reaction mixture, thereby forming additional molecular species containing bromine and nitrogen atoms. Such postulated in situ transformation of molecular species containing chlorine and nitrogen atoms into additional molecular species containing bromine and nitrogen atoms, however it takes place, requires a period of time to occur. Thus, in accordance with this theory, the minimum period of time is that required for such transformation to occur. In effect it is theorized, therefore, that this time period is a period in which there is, in the reaction mixture, an increase in the mole ratio of molecular species containing bromine and nitrogen atoms to molecular species containing chlorine and nitrogen atoms. Irrespective of the chemical reaction(s) or transformation(s) that actually occur in the reaction mixture during the period of time, the net result is deemed to be an increase in microbiocidal effectiveness. Since there does not appear to be, within reason, any upper limit on the duration of this period of time, one should maintain these pH conditions for a period that is long enough to ensure improved microbiocidal effectiveness. The minimum time period thus may be in terms of minutes or in terms of hours. The upper limit however is a matter of practicality and ordinarily one would not envision keeping the reaction mixture under these reduced pH conditions for more than, say, about 24 hours, although longer periods are within the purview and scope of this invention.

In the conduct of Section IV) the same alkali metal bases are used in the same manner as the bases used to raise the pH of the concentrated liquid biocide compositions as described above under PART ONE. Preferably the base used pursuant to Section IV) is the same species of base as used pursuant to Section II) above. For example if the base used pursuant to Section II) is sodium hydroxide, then it is preferable to use sodium hydroxide in conducting Section IV).

Operations pursuant to Sections I), II), III) and IV) are typically performed under the same temperature conditions as used in the other embodiments of this invention. For example, it is desirable to perform these operations at ambient room temperature or with some cooling to below room temperature. Thus temperatures in the range of about 25 to about 35° C. are recommended for these operations, although still lower temperatures can be used, if desired.

It will be appreciated that although the embodiments in PART TWO may result in somewhat greater attack upon the glass in glass-lined reaction vessels, the other advantages of PART ONE are achievable in PART TWO. These include minimal, if any, conversion of sulfamate to sulfate, and the ability to form concentrated liquid biocide compositions of enhanced microbiological effectiveness.

Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients, or if formed in solution, as it would exist if not formed in solution, all in accordance with the present disclosure. It matters not that a substance, component or ingredient may have lost its original identity through a chemical reaction or transformation during the course of such contacting, blending, mixing, or in situ formation, if conducted in accordance with this disclosure.

Each and every patent or publication referred to in any portion of this specification is incorporated into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of producing a concentrated liquid biocide composition, which process comprises:

A) bringing together in any feasible manner to form a reaction mixture (a) bromine atoms and chlorine atoms in the form of one or more of (i) bromine chloride, (ii) elemental bromine, and (iii) elemental chlorine, (b) a source of sulfamate anions, (c) alkali metal base, and (d) water, such that the numerical ratio of bromine atoms to chlorine atoms brought to the mixture is in the range of about 0.7:1 to about 1.7:1; and B) providing before and/or during A) enough alkali metal base in the mixture being formed in A) to keep the pH of such mixture in the range of about 7 to about 11 during all or substantially all of the time feeding in A) is occurring, the amounts of (a), (b), (c), and (d) used being amounts that form an active-bromine-containing solution in which (i) the active bromine content is at least about 50,000 ppm (wt/wt) and (ii) the atom ratio of nitrogen to active bromine originating from (a) and (b) is greater than about 0.93; and wherein if any sulfate is present in the active-bromine-containing solution as formed, such sulfate content is such that the molar ratio of sulfate to sulfamate in the solution is less than about 0.2.

2. A process according to claim 1 wherein (b) is an alkali metal sulfamate, wherein the alkali metal base referred to in A) and B) is a sodium base, and wherein said atom ratio of nitrogen to active bromine is greater than about 1.

3. A process according to claim 1 wherein (b) is sodium sulfamate, wherein the alkali metal base referred to in A) and B) is sodium hydroxide and/or sodium oxide, and wherein said atom ratio of nitrogen to active bromine is greater than about 1.

4. A process according to any of claims 1, 2, or 3 wherein said active bromine content is at least about 100,000 ppm.

5. A process according to any of claims 1, 2, or 3 wherein said active bromine content is at least about 120,000 ppm.

6. A process according to any of claims 1, 2, or 3 wherein said molar ratio of sulfate to sulfamate is less than about 0.05.

7. A process of producing a concentrated liquid biocide composition, which process comprises:
   A) feeding (a) bromine atoms and chlorine atoms in the form of one or more of (i) bromine chloride, (ii) elemental bromine, and (iii) elemental chlorine into (b) water containing sulfamate anions, or feeding each of (a) and (b) into a reaction vessel, such that the numerical ratio of the total number of bromine atoms fed to the total number of chlorine atoms fed is in the range of about 0.7:1 to about 1.7:1;
   B) providing before and/or during A) enough alkali metal base in the mixture being formed in A) to keep the pH of such mixture in the range of about 7 to about 11 during all or substantially all of the time feeding in A) is occurring, the amounts of (a), (b), (c), and (d) used being amounts that form an active-bromine-containing solution in which (i) the active bromine content is at least about 50,000 ppm (wt/wt), and (ii) the atom ratio of nitrogen to active bromine originating from (a) and (b) is greater than about 0.93; and wherein if any sulfate is present in the active-bromine-containing solution as formed, such sulfate content is such that the molar ratio of sulfate to sulfamate in the solution is less than about 0.2.

8. A process according to claim 7 wherein at least a portion of said alkali metal base provided in accordance with B) is provided by feeding a solution of alkali metal base to the mixture being formed in A).

9. A process according to claim 7 wherein at least a portion of said alkali metal base provided in accordance with B) is provided by having water-soluble alkali metal base in (b).

10. A process according to claim 7 wherein a portion of said alkali metal base provided in accordance with B) is provided by feeding a solution of alkali metal base to the mixture being formed in A), and wherein a portion of said alkali metal base provided in accordance with B) is provided by having water-soluble alkali metal base in (b).

11. A process according to claim 7 wherein pursuant to B) the pH of the mixture being formed in A) is kept in the range of about 8 to about 10 during all or substantially all of the time feeding in A) is occurring.

12. A process according to claim 11 wherein at least a portion of said alkali metal base provided in accordance with B) is provided by feeding a solution of alkali metal base to the mixture being formed in A).

13. A process according to claim 11 wherein at least a portion of said alkali metal base provided in accordance with B) is provided by having water-soluble alkali metal base in (b).

14. A process according to claim 11 wherein a portion of said alkali metal base provided in accordance with B) is provided by feeding a solution of alkali metal base to the mixture being formed in A), and wherein a portion of said alkali metal base provided in accordance with B) is provided by having water-soluble alkali metal base in (b).

15. A process according to any of claims 7, 8, 9, 10, 11, 12, 13, or 14 wherein said alkali metal base is a sodium base, wherein the amounts of (a) and (b) used are such as to form an active-bromine-containing solution in which (i) the active bromine content is at least about 100,000 ppm (wt/wt), and (ii) the atom ratio of nitrogen to active bromine originating from (a) and (b) is greater than about 1; and wherein if any sulfate is present in the solution as formed, such sulfate content is such that the molar ratio of sulfate to sulfamate in the solution is less than about 0.05.

16. A process of producing a concentrated liquid biocide composition, which process comprises:
   A) feeding (a) bromine atoms and chlorine atoms in the form of one or more of (i) bromine chloride, (ii) elemental bromine, and (iii) elemental chlorine into (b) water containing sulfamate anions, or feeding each of (a) and (b) into a reaction vessel, such that the numerical ratio of the total number of bromine atoms fed to the total number of chlorine atoms fed is in the range of about 0.7:1 to about 1.7:1; and
   B) providing before and/or during A) enough alkali metal base in the mixture being formed in A) to keep the pH of such mixture in the range of about 7 to about 11 during all or substantially all of the time feeding in A) is occurring, the amounts of (a), (b), (c), and (d) used being amounts that form an active-bromine-containing solution in which (i) the active bromine content is at least about 50,000 ppm (wt/wt), and (ii) the atom ratio of nitrogen to active bromine originating from (a) and (b) is greater than about 0.93; and wherein if any sulfate is present in the active-bromine-containing solution as formed, such sulfate content is such that the molar ratio of sulfate to sulfamate in the solution is less than about 0.2; and
   C) raising the pH of the active-bromine-containing solution so formed to at least about 12 by mixing additional alkali metal base therewith.

17. A process according to claim 16 wherein in C) the pH is raised at least to a pH in the range of about 13 to about 13.5.

18. A process according to claim 16 wherein at least a portion of said alkali metal base provided in accordance with B) is provided by feeding a solution of a sodium base to the mixture being formed in A).

19. A process according to claim 16 wherein at least a portion of said alkali metal base provided in accordance with B) is provided by having water-soluble sodium base in (b).

20. A process according to claim 16 wherein a portion of said alkali metal base provided in accordance with B) is provided by feeding a solution of a sodium base to the mixture being formed in A), and wherein a portion of said alkali metal base provided in accordance with B) is provided by having water-soluble sodium base in (b).

21. A process according to claim 16 wherein at least a portion of said alkali metal base provided in accordance with B) is provided by feeding a solution of sodium hydroxide to the mixture being formed in A).

22. A process according to claim 16 wherein at least a portion of said alkali metal base provided in accordance with B) is provided by having sodium hydroxide in (b).

23. A process according to claim 16 wherein a portion of said alkali metal base provided in accordance with B) is provided by feeding a solution of sodium hydroxide to the mixture being formed in A), and wherein a portion of said alkali metal base provided in accordance with B) is provided by having sodium hydroxide in (b).

24. A process according to claim 16 wherein pursuant to B) the pH of the mixture being formed in A) is kept in the range of about 8 to about 10 during all or substantially all of the time feeding in A) is occurring.

25. A process according to claim 24 wherein at least a portion of said alkali metal base provided in accordance with B) is provided by feeding a solution of sodium hydroxide to the mixture being formed in A).

26. A process according to claim 24 wherein at least a portion of said alkali metal base provided in accordance with B) is provided by having sodium hydroxide in (b).

27. A process according to claim 24 wherein a portion of said alkali metal base provided in accordance with B) is provided by feeding a solution of sodium hydroxide to the mixture being formed in A), and wherein a portion of said alkali metal base provided in accordance with B) is provided by having sodium hydroxide in (b).

28. A process according to any of claims 16, 17, or 24 wherein the numerical ratio of the total number of bromine atoms fed to the total number of chlorine atoms fed in accordance with A) is in the range of about 1:1 to about 1.2:1, wherein said alkali metal base provided in accordance with B) is sodium hydroxide, sodium oxide, or sodium carbonate, wherein said additional alkali metal base in C) is the same kind of sodium base as the base provided in accordance with B), wherein the amounts of (a) and (b) used are such that said active bromine-containing solution has (i) an active bromine content of at least about 100,000 ppm (wt/wt), and (ii) an atom ratio of nitrogen to active bromine originating from (a) and (b) that is greater than about 1.

29. A process according to claim 28 wherein the sodium base provided in accordance with B) is sodium hydroxide, wherein the additional sodium base in C) is sodium hydroxide, wherein said active bromine content of said active-bromine-containing solution is in the range of about 120,000 to about 160,000 ppm (wt/wt), and wherein if any sulfate is present in the solution as formed, such sulfate content is such that the molar ratio of sulfate to sulfamate in the solution is less than about 0.05.

30. A process according to claim 16 wherein the bromine atoms and chlorine atoms are fed in the form of (i) bromine chloride by itself, (ii) bromine chloride in a mixture with bromine, or (iii) bromine and chlorine fed separately and concurrently, and/or fed separately and sequentially with either one being fed first.

31. A process of minimizing or eliminating loss of sulfamate during production of a sulfamate-stabilized liquid biocide composition, which process comprises:
   A) feeding (a) bromine atoms and chlorine atoms in the form of one or more of (i) bromine chloride, (ii) elemental bromine, and (iii) elemental chlorine into (b) water containing sulfamate anion, or feeding each of (a) and (b) separately into a reaction vessel, or otherwise bringing (a) and the components of (b) together by feeding them in any way except feeding the components of (b) singly or in any combination into (a); and
   B) minimizing sulfate formation in the resultant aqueous solution by providing before and/or during A) enough alkali metal base in the mixture being formed in A) to keep the pH of the mixture in the range of about 7 to about 11 during all or substantially all of the time the feeding of A) is occurring so that if any sulfate is formed and is present, the molar ratio of sulfate to sulfamate in said resultant aqueous solution as formed is less than about 0.2.

32. A process according to claim 31 further comprising raising the pH of said resultant aqueous solution to at least about 12 by mixing additional alkali metal base therewith.

33. A process according to claim 32 wherein the pH of said resultant aqueous solution is raised at least to a pH that is in the range of about 13 to about 13.5.

34. A process according to either of claims 31 or 33 wherein the pH of the mixture being formed in A) is kept in the range of about 8 to about 10 during all or substantially all of the time the feeding of A) is occurring.

35. A process according to either of claims 31 or 33 wherein the proportions of (a) and (b) fed are such that the numerical ratio of the total number of bromine atoms fed to the total number of chlorine atoms fed is in the range of about 0.7:1 to about 1.7:1.

36. A process according to claim 35 wherein said numerical ratio is in the range of about 1:1 to about 1.2:1.

37. A process according to either of claims 31 or 33 wherein the proportions of (a) and (b) fed are such that said resultant aqueous solution has (i) an active bromine content of at least about 50,000 ppm (wt/wt), and (ii) an atom ratio of nitrogen to active bromine originating from (a) and (b) that is greater than about 1.

38. A process according to claim 37 wherein said active bromine content is at least about 100,000 ppm (wt/wt).

39. A process according to either of claims 31 or 33 wherein the proportions of (a) and (b) fed are such that (1) the numerical ratio of the total number of bromine atoms fed to the total number of chlorine atoms fed is in the range of about 1:1 to about 1.2:1, and (2) the active bromine content of said resultant aqueous solution is at least about 100,000 ppm (wt/wt), and (3) said resultant aqueous solution has an atom ratio of nitrogen to active bromine originating from (a) and (b) that is greater than about 1; and wherein if sulfate is present, the molar ratio of sulfate to sulfamate in said resultant aqueous solution as formed is less than about 0.05.

40. A process according to claim 31 wherein said alkali metal base provided in accordance with B) is a sodium base.

41. A process according to claim 33 wherein said alkali metal base provided in accordance with B) is sodium hydroxide, sodium oxide, or sodium carbonate, and wherein said additional alkali metal base in C) is the same kind of alkali metal base as used in B).

42. A process according to claim 33 wherein said alkali metal base provided in accordance with B) is sodium hydroxide, and wherein said additional alkali metal base in C) is sodium hydroxide.

43. A process of producing a concentrated liquid biocide composition, which process comprises:
   I) bringing together in any feasible manner to form a reaction mixture (a) bromine atoms and chlorine atoms in the form of one or more of (i) bromine chloride, (ii) elemental bromine, and (iii) elemental chlorine, (b) a source of sulfamate anions, (c) alkali metal base, and (d) water, such that (1) the numerical ratio of bromine atoms to chlorine atoms brought into the mixture is in the range of about 0.7:1 to about 1.7:1, and (2) the atom ratio of nitrogen to active bromine originating from (a) and (b) is greater than about 0.93; to form an active-bromine-containing reaction product mixture that has an initial pH over 11;
   II) providing before and/or during the conduct of I) an amount of alkali metal base in relation to the total amount of acid co-product(s) to be formed in the reaction, that results in the pH of such reaction product mixture decreasing by at least 1 pH unit during the conduct of I), to a pH in the range of about 7 to about 11;
   III) keeping the reaction mixture at a pH in the range of about 7 to about 11 for a period of time that increases the microbiocidal effectiveness of the concentrated liquid biocide composition being formed; and then
   IV) raising the pH of the resultant active-bromine-containing reaction product mixture to at least about 12 by mixing additional alkali metal base therewith.

44. A process according to claim 43 wherein (b) is an alkali metal sulfamate, wherein (c) is a sodium base, wherein said atom ratio of nitrogen to active bromine is greater than about 1, wherein said initial pH is at least about 12, and wherein the pH of said resultant active-bromine-containing reaction product mixture is raised to a pH that is at least in the range of about 13 to about 13.5.

45. A process according to claim 43 wherein (b) is sodium sulfamate, wherein the alkali metal base referred to in I), II), and IV) is sodium hydroxide, and wherein the pH of said resultant active-bromine-containing reaction product mixture is raised to a pH that is at least in the range of about 13 to about 13.5.

46. A process according to any of claims 43, 44, or 45 wherein in accordance with II) the pH of such reaction product mixture decreases by at least 2 pH units to a pH in the range of about 8 to about 10, and wherein in accordance with III) the reaction mixture is kept at a pH in the range of about 8 to about 10 for said period of time.

47. A process according to any of claims 43, 44, or 45 wherein said numerical ratio of bromine atoms to chlorine atoms is in the range of about 1:1 to about 1.2:1.

48. A process according to any of claims 43, 44, or 45 wherein said numerical ratio of bromine atoms to chlorine atoms is in the range of about 1:1 to about 1.2:1, wherein in accordance with II) the pH of such reaction product mixture decreases by at least 2 pH units to a pH in the range of about 8 to about 10, and wherein in accordance with III) the reaction mixture is kept at a pH in the range of about 8 to about 10 for said period of time.

49. A process of producing a concentrated liquid biocide composition, which process comprises:

I) feeding (a) bromine atoms and chlorine atoms in the form of one or more of (i) bromine chloride, (ii) elemental bromine, and (iii) elemental chlorine, into (b) an aqueous solution of sulfamate anions and alkali metal base, or feeding each of (a) and (b) into a reaction vessel, such that the numerical ratio of bromine atoms to chlorine atoms fed is in the range of about 0.7:1 to about 1.7:1 to form an active-bromine-containing reaction product mixture having an initial pH over 11;

II) providing before and/or during the feeding in I) an amount of alkali metal base in relation to the total amount of acid co-product(s) to be formed in the reaction, that results in the pH of such reaction product mixture decreasing by at least 1 pH unit during the feeding in I), to a pH in the range of about 7 to about 11;

III) keeping the reaction product mixture at a pH in the range of about 7 to about 11 for a period of time that increases the microbiocidal effectiveness of the concentrated liquid biocide composition being produced; and then IV) raising the pH of the resultant active-bromine-containing reaction product mixture to at least about 12 by mixing additional alkali metal base therewith.

50. A process according to claim 49 wherein said numerical ratio of bromine atoms to chlorine atoms referred to in I) is in the range of about 1:1 to about 1.2:1.

51. A process according to claim 49 wherein said initial pH of the active-bromine-containing reaction product mixture referred to in I) is at least about 12.

52. A process according to claim 49 wherein said initial pH of the active-bromine-containing reaction product mixture referred to in I) is at least about 13.

53. A process according to claim 49 wherein the decrease of the pH referred to in II) is a decrease to a pH in the range of about 8 to about 10.

54. A process according to claim 49 wherein the decrease of the pH referred to in II) is a decrease of at least 2 pH units.

55. A process according to claim 49 wherein the decrease of the pH referred to in II) is a decrease of at least 3 pH units.

56. A process according to claim 49 wherein the decrease of the pH referred to in II) is a decrease of at least 2 pH units to a pH in the range of about 8 to about 10.

57. A process according to claim 49 wherein the decrease of the pH referred to in II) is a decrease of at least 3 pH units to a pH in the range of about 8 to about 10.

58. A process according to claim 49 wherein the decrease of the pH referred to in II) is a decrease to a pH in the range of about 8 to about 10, and wherein pursuant to III) the reaction product mixture is kept at a pH in the range of about 8 to about 10.

59. A process according to claim 49 wherein in IV) the pH of the resultant active-bromine-containing reaction product mixture is raised to a pH that is at least in the range of about 13 to about 13.5.

60. A process according to claim 49 wherein said numerical ratio of bromine atoms to chlorine atoms referred to in I) is in the range of about 1:1 to about 1.2:1, wherein in IV) the pH of the resultant active-bromine-containing reaction product mixture is raised to a pH that is at least in the range of about 13 to about 13.5.

61. A process according to any of claims 49, 50, 59, or 60 wherein the alkali base referred to in I), in II), and in IV) consists essentially of sodium hydroxide, and wherein if in IV) sulfate is present in said resultant active-bromine-containing reaction product mixture as formed, the molar ratio of sulfate to sulfamate in said resultant active-bromine-containing reaction product mixture is less than about 0.2.

* * * * *